United States Patent [19]

Manley et al.

[11] Patent Number: 4,579,862

[45] Date of Patent: Apr. 1, 1986

[54] CERTAIN 1H-IMIDAZOL-1-YL-1-LOWER-ALKANOIC ACID DERIVATIVES HAVING ANTI-THROMBOTIC ACTIVITY

[75] Inventors: Paul W. Manley, Monks Risborough; Lai M. Fook, Maidenhead Berks, both of England

[73] Assignee: G. D. Searle & Co., Skokie, Ill.

[21] Appl. No.: 510,782

[22] Filed: Jul. 5, 1983

[51] Int. Cl.$^4$ ............... C07D 233/60; C07D 233/61; A61K 31/415
[52] U.S. Cl. .................................... 514/399; 546/339; 546/341; 546/342; 544/158; 544/162; 544/170; 548/341
[58] Field of Search ............... 548/341; 424/273 R; 514/399

[56] References Cited

U.S. PATENT DOCUMENTS

| | | | |
|---|---|---|---|
| 3,914,427 | 10/1975 | Kramer et al. | 514/399 |
| 4,036,970 | 7/1977 | Walker et al. | 514/399 |
| 4,215,220 | 7/1980 | Richter et al. | 548/341 |
| 4,229,459 | 10/1980 | Kramer et al. | 514/383 |

FOREIGN PATENT DOCUMENTS 2054560A 2/1981 United Kingdom ............... 514/341

*Primary Examiner*—Alan L. Rotman
*Attorney, Agent, or Firm*—Steven M. Odre

[57] ABSTRACT

Compounds of the general formula

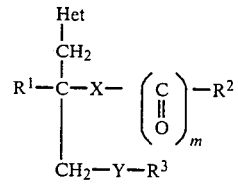

and pharmaceutically acceptable salts thereof have anti-thrombotic activity. Het represents 1-[1H-imidazolyl], 1-N-morpholinyl or pyridyl. A representative compound is 6-[2-(1H-Imidazol-1-yl)-1-yl-1-[[(4-methoxyphenyl)methoxy]methyl]ethoxy]hexanoic acid.

17 Claims, No Drawings

CERTAIN 1H-IMIDAZOL-1-YL-1-LOWER-ALKANOIC ACID DERIVATIVES HAVING ANTI-THROMBOTIC ACTIVITY

This invention relates to heterocyclic group-containing compounds having antithrombotic activity to the production thereof, and to compositions containing them, as well as to their use in therapy.

We have found that antithrombotic activity is possesed by heterocyclic derivatives of the general formula (I)

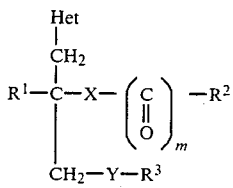

and pharmaceutically acceptable salts thereof in which $m = 0$ or $1$;

Het represents 1-[1H-imidazolyl], 1-N-morpholinyl, or pyridyl;

$R^1$ represents hydrogen or alkyl $C_1$-$C_6$;

$R^2$ represents an alkyl group ($C_1$-$C_{10}$, a straight or branched chain), optionally incorporating unsaturated carbon-carbon bonds and/or optionally interrupted with a heteroatom chosen from O, S, or $NR^1$ and which may be terminally substituted with a group selected from halogen, $OR^1$, $S(=O)_nR^1$ ($n = 0$-$2$), $COR^1$, $COOR^1$, $CONHR^1$, $CON(R^1)_2$, $NHR^1$ or $N(R^1)_2$ (in which $R^1$ has the meanings hereinbefore defined); and additionally, when Het is other than 1-[1H-imidazolyl], or when X represents $CH_2$, or $NR^1$, $R^2$ may additionally represent $CH_2R^4$ in which $R^4$ represents a phenyl ring which may or may not be substituted with one or more groups selected from $OR^1$, $S(=O)_nR^1$ ($n = 0$-$2$), $COR^1$, $COOR^1$, $CONHR^1$, $CON(R^1)_2$, $NHR^1$ or $N(R^1)_2$ (in which $R^1$, has the meanings hereinbefore defined);

$R^3$ represents an alkyl group ($C_1$-$C_{10}$ straight or branched chain) optionally containing unsaturated carbon-carbon bonds and which may be terminally substituted with $OR^1$ or $SR^1$ (in which $R^1$ has the meaning given above); or a group $CH_2R^5$ in which $R^5$ represents a phenyl ring which may or may not be substituted with one or more groups selected from halogen, $OR^1$, $(S=O)_nR^1$ ($n = 0$-$2$), $COR^1$, $COOR^1$, $CONHR^1$, $CON(R^1)_2$, $NHR^1$ or $N(R^1)_2$ (in which $R^1$ has the meanings hereinbefore defined); and additionally when $R^2$ is other than H, $R^3$ may additionally represent H;

X represents $CH_2$, O, S, or $NR^1$;

Y represents O, S or $NR^1$; and additionally, when Het is other than 1-[1H-imidazolyl], Y may additionally represent $CH_2$; and additionally when Het represents 1H-Imidazol-1-yl, Y may additionally represent $CH_2$ with the provisos that either X is $CH_2$ or $NR^1$ or $R^2$ specifically represents Substituted alkyl or benzyl ($CH_2R^4$) (substituents defined as hereinbefore).

The compounds of formula (I) contain one or more asymmetric centres. Formula (I) and other formulae in the specification embrace all stereoisomers represented therein. In particular such formulae include the enantiomeric forms, such mixtures as are designated racemates, and diastereoisomers.

The invention therefore provides heterocyclic derivatives of formula I, with pharmaceutically acceptable salts, as well as all stereoisomers as mentioned above.

In the compounds of the invention Het preferably represents 1-[1H-imidazolyl], 2-pyridyl, 3-pyridyl, 4-pyridyl or 1-N-morpholinyl.

$R^2$ may represent a straight $C_{1-10}$ alkyl chain (e.g. n-butyl, n-pentyl, n-hexyl), a branched $C_{1-10}$ alkyl chain (e.g. 5,5-dimethylpentyl), a $C_{1-10}$ alkenyl chain (e.g. 3-butenyl, 4-pentenyl, 5-hexenyl), a $C_{1-10}$ branched alkenyl chain (e.g. 5-methyl-4-pentenyl) or a $C_{1-10}$ alkynyl chain (e.g. 3-butynyl, 4-pentynyl or 5-hexynyl), any of which may be interrupted with a group O, S or $NR^1$ (e.g. ethoxyethyl). Preferred numbers of carbon atoms are four to six for a straight alkyl, alkenyl or alkynyl chain and six to eight for a branched alkyl, alkenyl or alkynyl chain. Compounds in which $R^2$ is interrupted with O, S or $NR^1$ are preferred when X represents $CH_2$, and preferred interrupting groups are O, S, and $NR^1$ where $R^1$ preferably represents hydrogen or methyl. Preferred compounds are those in which $R^2$ is terminally substituted with a group selected from halogen, $OR^1$, $S(=O)_nR^1$ ($n = 0$-$2$), $COR^1$, $COOR^1$, $CONHR^1$, $CON(R^1)_2$, $NHR^1$ or $N(R^1)_2$ in which $R^1$ is preferably hydrogen or a $C_{1-6}$ alkyl groups. Particularly preferred substituent groups are $COOR^1$, $CONHR^1$ and $CON(R^1)_2$.

Thus a particularly preferred group of compounds are those in which $R^2$ represents a $C_{4-8}$ straight chain or branched chain alkyl, alkenyl or alkynyl group terminally substituted with a group $COOR^1$, $CONHR^1$ or $CON(R^1)_2$. Examples of such groups are $(CH_2)_5COOH$, $(CH_2)_5COOCH_2CH_3$, $(CH_2)_5COOCH_2C(CH_3)_3$, $(CH_2)_4C(CH_3)_2COOH$, cis- and trans-$(CH_2)_3CH=CHCOOH$ and cis- and trans-$(CH_2)_3CH=CHCOOCH_2CH_3$.

With certain provisos $R^2$ may also represent a benzyl group $CH_2R^4$ in which $R^4$ represents a phenyl ring which may or may not be substituted with one or more groups selected from $OR^1$, $S(=O)_nR^1$ ($n = 0$-$2$), $COR^1$, $COOR^1$, $CONHR^1$, $CON(R^1)_2$, $NHR^1$ or $N(R^1)_2$. Preferred substituent groups in this meaning are $OR^1$, $SR^1$, $COOR^1$, $CONHR^i$ and $CON(R^1)_2$. Examples of particularly preferred benzyl groups $CH_2R^4$ are 4-$CH_2C_6H_4OCH_3$, 4-$CH_2C_6H_4SCH_3$, 4-$CH_2C_6H_4COOH$, 4-$CH_2C_6H_4COO(CH_2)_3CH_3$, 4-$CH_2C_6H_4CONHCH_3$ and 4-$CH_2C_6H_4CON(CH_3)_2$.

In the above definitions $R^3$ may represent a straight or branched chain alkyl, alkenyl or alkynyl group. Such groups contain one to ten carbon atoms, preferably one to eight carbon atoms in the case of a straight chain and six to ten carbon atoms in the case of a branched chain. $R^3$ may be terminally substituted with the groups $OR^1$ or $SR^1$ where $R^1$ is preferably hydrogen or methyl. The group $R^3$ may also represent a benzyl group $CH_2R^5$ in which $R^5$ is a substituted or unsubstituted phenyl ring. Examples of such benzyl groups are $CH_2C_6H_5$, 4-$CH_2C_6H_4Br$, 4-$CH_2C_6H_4OCH_3$, 4-$CH_2C_6H_4COOH$, 4-$CH_2C_6H_4$-$COOCH_2CH_3$, 4-$CH_2C_6H_4CON(CH_3)_2$, and 4-$CH_2C_6H_4N(CH_3)_2$.

The group X, preferably represents O, S, $CH_2$ or $NR^1$ in which $R^1$ is preferably hydrogen or methyl. The group Y preferably represents O, S, or $NR^1$ where $R^1$ is preferably hydrogen or methyl, and it may also represent CH$_2$ with certain provisos.

In a preferred aspect of the invention

Het represents 1-[1H-imidazolyl] or pyridyl;

R$^1$ represents hydrogen or methyl;

R$^2$ represents C$_{3-7}$ alkyl optionally incorporating unsaturated carbon-carbon bonds and/or optionally interrupted by O, S or NR$^1$, and substituted with OR$^1$, S(=O)$_n$R$^1$, COR$^1$, COOR$^1$, CONHR$^1$, CON(R$^1$)$_2$, NHR$^1$, or N(R$^1$)$_2$, wherein n and R$^1$ are as defined above;

R$^3$ is as defined above;

m=0;

X represents O, S, NH, NMe or CH$_2$; and

Y represents O, S, NH, NMe or CH$_2$.

In an alternative preferred aspect of the invention,

Het represents 3-pyridyl;

R$^1$ represents hydrogen or C$_{1-3}$ alkyl;

R$^2$ represents CH$_2$R$^4$ in which R$^4$ is as defined above;

R$^3$ represents hydrogen or CH$_2$R$^5$ where R$^5$ is as defined above;

m=0, 1;

X represents O, S, NH, NMe or CH$_2$; and

Y represents O, S, NH, NMe or with the provisos defined above Y may additionally represent CH$_2$.

In a most preferred aspect of the invention

Het represents 1H-imidazol-1-yl;

R$^1$ represents hydrogen;

R$^2$ represents C$_{4-8}$ alkyl incorporating unsaturated carbon-carbon bonds and substituted with COOR$^1$, CONHR$^1$, or CON(R$^1$)$_2$ wherein R$^1$ is as defined above;

R$^3$ is as defined above;

m=0;

X represents O, S, NH, NMe or CH$_2$; and

Y represents O, S, or CH$_2$.

Specific compounds according to the invention are those, the preparation of which is described in the Examples.

The compounds according to the invention have antithrombotic activity and are useful in treating disease states which involve platelet dysfunction or platelet hyperactivity, such as cerebrovascular disease, ischaemic heart disease, diabetic retinopathy, angina, peripheral vascular disease and myocardial infarction.

Chronic platelet dysfunction or hyperactivity of platelets is associated with many chronic diseases such as cerebrovascular disease, ischaemic heart disease, diabetic retinopathy, angina, peripheral vascular disease and myocardial infarction. Oral, long acting platelet therapy is useful in the prophylaxis and/or therapeutic treatment of such diseases.

Antiplatelet therapy is also useful to reduce complications from surgical procedures and aid in the maintenance of prosthetic devices, vascular catheters, heart valves, renal dialysis shunts and the apparatus used in cardiopulmonary bypass surgery.

Platelet activation results in the formation of platelet aggregates and the release of proaggregatory substances which increase platelet involvement and further the process of aggregation. Platelets are sensitive to many triggering substances and platelet activation may be initiated through several pathways depending upon the particular disease state. Such aggregatory stimuli as collagen, thromboxane A$_2$ (TXA$_2$), adenosine diphosphate (ADP), adrenaline, 5-hydroxytryptamine, thrombin or platelet activating factor (PAF) may either act directly on receptors resulting in platelet aggregation and/or may effect cAMP levels and/or Ca++ sequestration to produce platelet aggregation.

Consequently, compounds capable of inhibiting platelet activation induced by such agents as for example arachidonic acid, collagen and platelet activating factor have considerable clinical utility in medicine.

The antiaggregatory activity of the compounds of the invention may be demonstrated by their ability to inhibit in vitro human platelet response induced by agents such as arachidonic acid, collagen and platelet activating factor (PAF) measured, for example, turbidometrically according to the method first described by G. V. R. Born et al, Nature, (1962), 194, 927. In vivo activity in rabbits (i.v. or oral dosing) may be evaluated by measurement of inhibitory potency against collagen or PAF induced thrombocytopoenia using continuous platelet count monitoring according to the method of G. M. Smith and F. Freuler, Bibl.Anat., (1973), 12, 229.

The compounds of the general formula (I), according to the invention in which X is —O—, —S—, or —NR$^1$— in which R$^1$ has the meaning given hereinbefore may be prepared by reacting a compound of the formula (II):

in which Het, R$^1$, R$^3$, and Y are as hereinbefore defined and X represents —O—, —S—, or —NR$^1$— in which R$^1$ is as hereinbefore defined with a compound of the general formula (III):

in which L represents a nucleophilically displaceable group, for example a halogen atom such as chlorine, bromine or iodine (m=0,1), or a sulphonyloxy group (m=0) such as the methanesulphonyloxy or p-toluenesulphonyloxy group, and R$^2$ is defined as hereinbefore. The product may be isolated as the base or as an acid addition salt. The reaction is preferably carried out in the presence of a suitable base, for example, using an alkali metal hydride such as sodium hydride in an anhydrous aprotic organic solvent under an inert atmosphere, using potassium hydroxide in a solvent such as dimethyl sulphoxide, or in the cases in which X represents S or NR$^1$ using potassium carbonate in dimethylformamide.

The reaction may be conducted at ambient temperature (10°-20° C.) or at somewhat elevated temperature (of the order of 70° C.).

The compounds of formula (II) in which X is O or S may be prepared from the parent substituted oxirane or thiirane of the general formula (IV) in which X may be O or S—

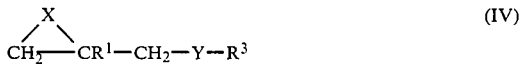

by reacting these with, for example, imidazole, or morpholine, which may be in the form of an alkali metal salt, such as the sodium salt, or for example with 2-, 3- or 4-lithopyridine in the presence of cuprous iodide trimethylphosphite complex at −100° C. in tetrahydrofuran.

Compounds of formula (II) in which X represents NH and Het, $R^3$ and Y are as defined hereinbefore, may be prepared by the reduction of compounds of formula (V) with suitable reducing agents, such as lithium aluminum hydride in an inert solvent such as tetrahydrofuran. The compounds of formula (V) may be

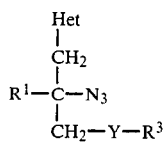
(V)

obtained by reaction of a compound of general formula (VI)

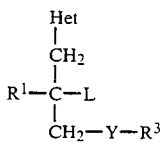
(VI)

in which L is a sulphonyloxy group such as the methanesulphonyloxy or p-toluenesulphonyloxy group and Het, $R^1$, $R^3$ and Y as defined hereinbefore, with an alkali metal azide, for example sodium azide in an aprotic solvent at elevated temperature (for example dimethylformamide at 70° C.).

Compounds of general formula (VI) may be prepared from the compounds of formula (II) in which X represents O, and Het, $R^1$, $R^3$ and Y are as hereinbefore defined, with either methane sulphonyl chloride or p-toluene sulphonyl chloride using standard conditions.

Compounds of the formula (II) in which X represents $NR^1$ in which $R^1$ is lower alkyl $C_1$-$C_4$ may be prepared by reductive alkylation of compounds of formula (II) in which X represents NH, with an aldehyde (for example formaldehyde when $R^1$ in $NR^1$ represents $CH_3$, or acetaldehyde when $R^1$ represents $CH_2CH_3$) in the presence of a suitable reducing agent such as sodium cyanoborohydride.

The thiiranes of formula (IV) in which X represents S, and $R^1$, Y, and $R^3$ as defined as hereinabove, may be prepared from the corresponding oxiranes of formula (V) in which X represents O, by treating them with triphenylphosphine sulphide in the presence of trifluoroacetic acid in toluene.

The oxiranes of formula (IV) in which X represents O, Y represents O, S, or $NR^1$, and $R^1$ and $R^3$ are defined as hereinbefore, may be obtained by reacting an epihalohydrin of the formula (VII) in which Hal represents Cl or Br

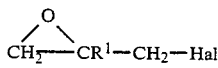
(VII)

with a compound of the formula (VIII)

 (VIII)

in which Y and $R^3$ are as hereinbefore defined, preferably in the presence of a suitable base such as sodium hydride when Y represents O, or potassium carbonate when Y represents S or $NR^1$.

The oxiranes of formula (IV), in which X represents O, and Y represents $CH_2$, may be prepared by reacting alkenes of general formula (IX) in which $R^1$ and $R^3$ are defined as hereinbefore with

(IX)

m-chloroperbenzoic acid in dichloromethane. Compounds of formula (IX) may be prepared by reacting haloalkenes of formula (X)

(X)

in which $R^1$ is defined as hereinbefore and Hal represents Cl or Br with Grignard reagents $R^3MgHal$ in which $R^3$ is as hereinbefore defined and Hal represents Cl, Br or I, in a suitable solvent such as diethyl ether or tetrahyrofuran.

Compounds of general formula (I) in which $X=Y=CH_2$ and $m=0$, may be prepared by reacting a compound of formula (XI),

(XI)

in which L represents a nucleophilically displaceable group, for example a halogen atom such as chlorine, bromine or iodine or a sulphonyloxy group such as a methanesulphonyloxy group, and $R^1$, $R^2$ and $R^3$ are defined as hereinbefore, with, for example imidazole, or morpholine, which may be in the form of an alkali metal salt, such as the sodium salt, or for example with 2-, 3-, or 4-lithopyridine in the presence of cuprous iodide trimethylphosphite complex at −100° C. in tetrahyrofuran.

The compounds of general structure (XI) may be obtained from the corresponding alcohol of formula (XII) in which $R^1$, $R^2$ and $R^3$ have the meanings given hereinbefore by reaction

(XII)

with a suitable reagent. Thus if L represents chlorine a suitable reagent is thionyl chloride or if L represents methanesulphonyloxy a suitable reagent is methane sulphonylchloride in the presence of pyridine.

The alcohol of general formula (XII) may be obtained by the reduction of the corresponding acids of formula (XIII) with a suitable reducing agent, for example diborane in an inert solvent such as tetrahydrofuran.

(XIII)

The acids of general formula (XIII) may be prepared by reaction of compounds of formula (XIV) in which R¹

$$R^3—CH_2—CH_2—CHR^1—COOR \quad (XIV)$$

and R³ are defined as hereinbefore, with two equivalents of a suitable base, such as lithium diisopropylamide, followed by treatment with one equivalent of a compound of general formula R²CH₂L in which L is a suitable nucleophilically displaceable group such as a halogen and R² is defined as hereinbefore.

Alternatively, compounds of general formula (I) in which X=Y=CH₂ and R¹=H may be obtained by the reduction of compounds of formula (XV) in which Het, R² and R³

are defined as hereinbefore. A suitable reducing agent for this conversion is hydrogen in the presence of a catalyst such as 10% palladium on carbon in a solvent such as ethanol or acetic acid.

Compounds of formula (XV) may be prepared by the reaction of ketones of formula (XVI) with suitable compounds

such as the phosphonite of formula (XVII) in the presence of $$Ph_2P(=O)CH_2CH_2R^3 \quad (XVII)$$

a suitable base, for example n-butyl lithium in tetrahydrofuran.

Ketones of formula (XVI) may be prepared by reaction of iodides of formula R²CH₂COCH₂I with suitable heterocycles in the presence of base, for example imidazole, or morpholine in the form of an alkali metal salt such as the sodium salt, or for example with 2-, 3-, or 4-lithiopyridine in the presence of cuprous iodide trimethylphosphite complex in tetrahydrofuran. Iodides of formula RCH₂COCH₁I may be obtained by refluxing the corresponding chlorides R²CH₂COCH₂Cl with an excess of sodium iodide in acetone. Chlorides of the formula R²CH₂COCH₂Cl are prepared by reaction of the known acid chlorides R²CH₂COCl with diazomethane in diethyl ether followed by treatment with hydrogen chloride gas.

Phosphonites of formula (XVII) may be obtained from the corresponding compounds of formula R³CH₂CH₂L, in which L represents a halogen atom, such as bromine or iodine, by reaction with ethyl diphenyl phosphinite in an inert solvent, such as toluene at an elevated temperature, for example 80° C.

Compounds of general formula (I) in which X=CH₂, M=0, Y represents O, S, and R¹, R² and R³ are defined as hereinbefore, may be prepared by reacting a compound of general formula (XVIII) with

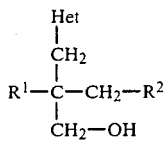

a compound of general formula L—R³ in which L represents a nucleophilically displaceable group, for example a halogen such as chlorine, bromine or iodine, or a sulphonyloxy group such as the methanesulphonyloxy group and R³ is defined as hereinbefore.

Compounds of formula (XVIII) in which Y=0 and Het, R¹ and R² are defined as hereinbefore may be obtained by

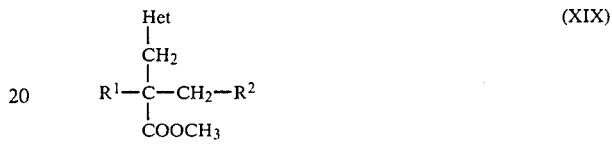

the reduction of the corresponding methyl ester of formula (XIX) with a suitable reducing agent, for example lithium aluminium hydride in an inert solvent such as tetrahydrofuran.

Compounds of general formula (I) in which X=CH₂, m=0, Y represents S or NR¹, and Het, R¹ and R² are defined as hereinbefore, may be prepared by reacting the compounds of general formula (XX) in which L represents a nucleophilically displaceable group

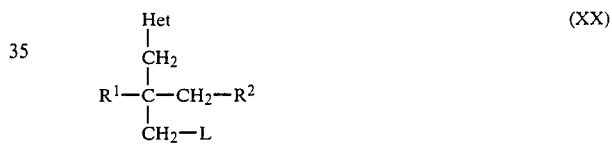

for example a halogen, such as chlorine, or a sulphonyloxy group such as the methanesulphonyloxy group, with a compound of formula R³YH, in which Y represents S or NR¹ and R¹ and R³ are defined as hereinbefore, in the presence of a suitable base such as potassium carbonate.

Compounds of general formula (XX) may be obtained by reaction of compounds of general formula (XVIII) in which Het, R¹ and R² are defined as hereinbefore with a suitable reagent. Thus if L represents chlorine a suitable reagent is thionyl chloride, or if L represents methanesulphonyloxy a suitable reagent is methanesulphonyl chloride in the presence of pyridine.

The esters of general formula (XIX) may be obtained from compounds of general formula (XXI), in which L represents a

nucleophilically displaceable group, for example a halogen atom, such as chlorine, bromine or iodine, or a sulphonyloxy group such as a methane sulphonyloxy group with for example imidazole, or morpholine, which may be in the form of an alkali metal salt, such as the sodium salt, or for example with 2-, 3-, or 4-lithiopyridine in the presence of cuprous iodide trimethylphosphite complex at −100°0 C. in tetrahydrofuran.

Compounds of formula (XXI) may be obtained from the corresponding alcohols of general formula (XXII) in

which $R^1$ and $R^2$ are defined as hereinbefore, by reaction with a suitable reagent. Thus if L represents chlorine a suitable reagent is thionyl chloride, or if L represents methanesulphonyloxy a suitable reagent is methanesulphonyl chloride.

The alcohols of general formula (XXII) may be prepared from the esters of general formula (XXIII), by

reaction with one equivalent of a suitable base, for example lithium diisopropylamide in a solvent such as tetrahydrofuran followed by treatment with formaldehyde.

In producing the compounds according to the invention, the groups $R^1$, $R^2$ and $R^3$ may be obtained by conversion of one group within the meaning given for that group to another meaning, by one or more process steps.

Thus, by way of example compounds in which $R^2$ represents an alkyl group terminally substituted with a $CON(R^1)_2$ group in which $R^1$ is hydrogen, this may be obtained from the parent carboxylic acid by reaction with ammonia. This amide may then if desired be converted to the amine by reduction. Also the parent carboxylic acid can be converted to an ester, for example an ethyl ester (COOEt) which may then be converted by reduction, for example with $LiAlH_4$, to the corresponding alcohol ($CH_2OH$). This can if so desired be oxidised the corresponding aldehyde (CHO) or alkylated, for example, methylated to the corresponding methyl ether ($CH_2OCH_3$).

In another conversion the group $R^3$ when this is a substituted benzyl group may be removed by hydrogenolysis to leave the compound in which $R^3$ is hydrogen.

Such conversions are carried out by conventional means and are among the processes exemplified in the Examples which follow.

For use as medicinal agents the compounds according to the invention may be administered by any suitable route, preferably in the form of a pharmaceutical composition adapted to such route, and in a dose effective for the treatment intended.

Accordingly, the invention provides a pharmaceutical composition comprising one or more compounds according to the invention in association with one or more non-toxic, pharmaceutically acceptable carriers and/or diluents and/or adjuvants and if desired other active ingredients. The composition may for example be applied orally or by injection.

For oral administration, the pharmaceutical composition may take the form of, for example, a tablet, capsule, suspension or liquid. The pharmaceutical composition is preferably made in the form of a dosage unit contained in a particular amount of the active ingredient. Examples of such dosage units are tablets or capsules. These may with advantage contain an amount of active ingredient from 5 to 250 mg preferably 25 to 150 mg. A suitable daily dose for a mammal may vary widely depending on the condition of the patient and other factors. However, a dose of from 0.1 to 300 mg/kg body weight, particularly 1 to 100 mg/kg body weight may be appropriate.

The active ingredient may also be administered by injection as a composition wherein, for example, saline, dextrose or water for injection may be used as a suitable carrier. A suitable daily dose of about 0.1 to 100 mg per kg body weight injected per day in multiple doses depending on the disease being treated. A preferred daily dose would be from 1 to 30 mg/kg body weight.

As indicated, the dose administered and the treatment regimen will be dependent, for example, on the disease, the severity thereof, on the patient being treated and his response to treatment and therefore may be widely varied.

The pharmaceutical compositions may be prepared by techniques well known in the art and described, inter alia, in Remington's Pharmaceutical Science, Mach Publishing Co., Easton, Penn., 1965.

The following Examples illustrate the invention:

EXAMPLE 1

6-[2-(1H-Imidazol-1-yl)-1-[[(4-methoxyphenyl)methoxy]methyl]ethoxy]hexanoic acid (a) 2,3-Epoxypropyl-4-methoxybenzyl ether A solution of 4-methoxybenzyl alcohol (800 g, 5.8 mol) in dry tetrahydrofuran (1200 ml) was added dropwise to a stirred slurry of sodium hydride (280 g of a 60% dispersion in oil, 7.0 mol) in dry tetrahydrofuran (600 ml) at −5° C. and under a gentle stream of dry nitrogen. The mixture was allowed to warm up to room temperature and stirred until hydrogen evolution ceased. The resulting slurry of the sodium alkoxide was cooled to −5° C. and treated with epibromohydrin (860 g, 6.3 mol) at a rate such that the temperature remained below 5° C. The reaction mixture was allowed to warm gradually to room temperature and left stirring for 12 hours.

The final mixture was filtered and washed with methanol. The combined filtrate and washings were evaporated to dryness under reduced pressure to afford the crude product (250 g). Further purification of this crude product by column chromatography (silica gel, chloroform) afforded 2,3-epoxypropyl-4-methoxybenzyl ether as a pale yellow oil.

$^1$H-NMR (δ-CDCl$_3$): 2.70 (m, 2H), 3.20 (m, 1H), 3.65 (m, 2H), 3.37 (s, 3H), 4.73 (s, 2H) and 7.15 (q, 4H).

(b) 1-[2-Hydroxy-3-[(4-methoxyphenyl)methoxy]propyl]-1H-imidazole 2,3-Epoxypropyl-4-methoxybenzyl ether (100 g, 0.515 mol) in dry tetrahydrofuran (200 ml) was treated with imidazole (44.4 g, 0.653 mol) and heated under reflux for 16 hours. The solution was filtered and the solvent was evaporated off under reduced pressure to give a brown solid which was recrystallised from 10% water-propan-1-ol to give 1-[2-hydroxy-3-[(4-methoxyphenyl)methoxy]propyl]-1H-imidazole as a colourless crystalline solid, m.p. 96°–98° C.

(c)

6-[2-(1H-Imidazol-1-yl)-1-[[(4-methoxyphenyl)methoxy]methyl]ethoxy]hexanoic acid 1-[2-Hydroxy-3-[(4-methoxyphenyl)methoxy]-propyl]-1H-imidazole (20 g, 0.076 mol) was added to a stirred suspension of powdered potassium hydroxide (17 g, 0.30 mol) in dimethylsulphoxide (50 ml) at 18° C. and stirred for 0.5 hours. Ethyl 6-bromohexanoate (33.45 g, 0.15 mol) was then added and the resulting mixture was stirred at 18° C. for 12 hours. The reaction mixture was diluted with water (2l) and washed with dichloromethane (2×100 ml), neutralised to pH 6–7 with sulphuric acid (2M) and extracted with dichloromethane (4×150 ml). The combined extracts were dried ($Na_2SO_4$) and the solvent was evaporated off under reduced pressure to give the crude product which by column chromatography (silica gel, 20% methanol in ethyl acetate) gave pure 6-[2-(1H-imidazol-1-yl)-1-[[(4-methoxyphenyl)methoxy]methyl]ethoxy]hexanoic acid as a colourless oil.

$^1$H-NMR ($\delta$-$CDCl_3$): 1.2–1.4 (M, 2H), 1.5–1.7 (m, 4H), 2.28 (t, 2H), 3.1–3.3 (m, 2H), 3.4–3.6 (m, 3H), 3.81 (s, 3H), 3.95–4.15 (m, 2H), 4.44 (ABq, 2H), 6.90 and 7.25 (ABq, 4H), 6.88 (s, 1H), 7.06 (s, 1H), 7.68 (s, 1H) and 9.7 (broad s, 1H).

EXAMPLE 2

5-[2-(1H-Imidazol-1-yl)-1-[[(4-methoxyphenyl)methoxy]methyl]ethoxy]pentanoic acid This compound was prepared as described in Example 1c but using ethyl 5-bromopentanoate. The crude product was purified by column chromatography (silica gel, 10% ethanol in chloroform) to give the title compound as a pale-yellow oil.

$^1$H-NMR ($\delta$-$CDCl_3$): 1.51–1.72 (m, 4H), 2.31 (m, 2H), 3.19–3.36 (m, 2H), 3.41–3.64 (m, 3H), 3.80 (s, 3H), 3.96–4.21 (m, 2H) 4.46 (s, 2H), 6.90 and 7.24 (ABq, 4H), 6.92 (s, 1H), 7.06 (s, 1H) and 8.72 (broad s, 1H).

EXAMPLE 3

7-[2-(1H-Imidazol-1-yl)-1-[[(4-methoxyphenyl)methoxy]methyl]ethoxy]heptanoic acid This compound was prepared as described in Example 1c but using ethyl 7-bromoheptanoate. The crude product was purified by column chromatography (silica gel, 10% ethanol in chloroform) to give the title compound as a pale-yellow oil.

$^1$H-NMR ($\delta$-$CDCl_3$): 1.2–1.7 (m, 8H), 2.30 (t, 2H), 3.24 (m, 2H), 3.4–3.6 (m, 3H), 3.81 (s, 3H), 3.95–4.15 (m, 2H), 4.45 (s, 2H), 6.96 and 7.24 (ABq, 4H), 6.97 (s, 1H), 7.08 (s, 1H), 7.70 (s, 1H), 8.84 (s, 1H).

EXAMPLE 4

Ethyl 6-[2-(1H-imidazol-1-yl)-1-[[(4-methoxyphenyl)methoxy]methyl]ethoxy]hexanoate A stirred solution of 6-[2-(1H-imidazol-1-yl)-1-[[(4-methoxyphenyl)methoxy]methyl]ethoxy]hexanoic acid (Example 1c) (10 g, 0.026 mol) and triethylamine (3.0 g, 0.03 mol.) in dichloromethane (100 ml, dried over 4A molecular sieves) at −50° C. was treated dropwise with ethyl chloroformate (3.2 g, 0.029 mol.). The solution was allowed to warm up to 0° C. over 0.5 hours, cooled back to −50° C. and treated with ethanol (6 ml, 0.1 mol). The solution was allowed to warm up and then stirred for 15 hours at 18° C. The mixture was then shaken with an aqueous solution of saturated sodium carbonate (500 ml). The organic layer was separated, dried ($Na_2SO_4$) and the solvent was evaporated off under reduced pressure to give the crude product which was purified by column chromatography (silica gel, 5% ethanol in chloroform) to give ethyl 6-[2-(1H-imidazol-1-yl)-1-[[(4-methoxyphenyl)methoxy]methyl]ethoxy]hexanoate as a pale-yellow oil.

$^1$H-NMR ($\delta$-$CDCl_3$): 1.20–1.35 (m, 2H), 1.26 (t, 3H), 1.44–1.68 (m, 4H), 2.27 (t, 2H), 3.22–3.36 (m, 2H), 3.52–3.64 (m, 1H), 3.81 (s, 3H), 3.94–4.20 (m, 4H), 4.45 (s, 2H), 6.90 and 7.28 (ABq, 4H), 6.91 (s, 1H), 7.02 (s, 1H), and 7.46 (s, 1H).

EXAMPLE 5

Ethyl 5-[2-(1H-Imidazol-1-yl)-1-[[(4-methoxyphenyl)methoxy]methyl]ethoxy]pentanoate This compound was prepared as in Example 4 using 5-[2-(1H-imidazol-1-yl)-1-[[(4-methoxyphenyl)methoxy]methyl]ethoxy]pentanoic acid (Example 2). The crude product was purified by column chromatography (silica gel, 5% ethanol in chloroform) to give the title compound as a pale-yellow oil.

$^1$H-NMR ($\delta$-$CDCl_3$): 1.22 (t, 3H), 1.42–1.69 (m, 4H), 2.2/ (t, 2H), 3.21–3.34 (m, 2H), 3.38–3.60 (m, 3H), 3.76 (s, 3H), 3.92–4.16 (m, 4H), 4.44 (s, 2H), 6.87 and 7.24 (ABq 4H), 6.93 (s, 1H), 7.00 (s, 1H), and 7.26 (s, 1H).

EXAMPLE 6

Ethyl 7-[2-(1H-imidazol-1-yl)-1-[[(4-methoxyphenyl)methoxy]methyl]ethoxy]heptanoate This compound was prepared as in Example 4 using 7-[2-(1H-imidazol-1-yl)-1-[[(4-methoxyphenyl)methoxy]methyl]ethoxy]heptanoic acid (Example 3). The crude product was purified by column chromatography (silica gel, 10% ethanol in chloroform) to give the title compound as a pale-yellow oil.

$^1$H-NMR ($\delta$-$CDCl_3$): 1.20–1.40 (m, 7H), 1.40–1.70 (m, 4H), 2.27 (t, 2H), 3.24–3.36 (m, 2H), 3.40–3.66 (m, 3H), 3.83 (s, 3H), 3.92–4.20 (m, 4H), 4.46 (s, 2H), 6.90 and 7.28 (ABq, 4H), 6.93 (s, 1H), 7.04 (s, 1H), and 7.49 (s, 1H).

EXAMPLE 7

Isopropyl 6-[2-(1H-imidazol-1-yl)-1-[[(4-methoxyphenyl)methoxy]methyl]ethoxy]hexanoate (a) Isopropyl 6-bromohexanoate A solution of ε-caprolactone (30 g) in 2-propanol (250 ml) at 0° C. was saturated with hydrogen bromide gas. Sulphuric acid (18M, 5 ml) was then added and the solution was heated under reflux for 16 hours. The reaction mixture was poured into water (200 ml), basified with sodium hydrogen carbonate, and extracted with diethyl ether. The combined extracts were dried ($Na_2SO_4$) and the solvent was evaporated off under reduced pressure to give the crude product which was purified by column chromatography (alumina, dichloromethane) to give isopropyl 6-bromohexanoate as a pale-yellow oil.

¹H-NMR (δ-CDCl₃): 1.22 (d, 6H), 1.40–1.58 (m, 2H), 1.58–1.74 (m, 2H), 1.80–1.95 (m, 2H) 2.21–2.38 (m, 2H), 3.32–3.48 (m, 2H) and 5.00 (m, 1H).

(b) Isopropyl-6-[2-(1H-imidazol-1-yl)-1-[[(4-methoxyphenyl)methoxy]methyl]ethoxy]hexanoate 1-[2-Hydroxy-3-[(4-methoxyphenyl)methoxy]propyl]-1H-imidazole (Example 1b; 10 g, 0.038 mol) was added to a stirred suspension of powdered potassium hydroxide (8 g, 0.14 mol) in dimethylsulphoxide (20 ml) at 18° C. and stirred for 0.5 hours. Isopropyl 6-bromohexanoate (10.5 g, 0.044 mol) was then added and the mixture was stirred for 0.5 hours at 18° C. The mixture was poured into saturated aqueous ammonium chloride (1500 ml) and extracted with dichloromethane. The combined extracts were dried (Na₂SO₄) and the solvent was evaporated off under reduced pressure to give the crude product which was purified by column chromatography (silica gel, 2% ethanol in chloroform) to give isopropyl 6-[2-(1H-imidazol-1-yl)-1-[[(4-methoxyphenyl)methoxy]methyl]ethoxy]hexanoate as a pale-yellow oil.

¹H-NMR (δ-CDCl₃): 1.22 (d, 6H), 1.20–1.72 (m, 6H), 2.25 (t, 2H), 3.23–3.52 (m, 4H), 3.58 (m, 1H), 3.82 (s, 3H), 3.94–4.20 (m, 2H), 4.46 (s, 2H), 5.00 (m, 1H), 6.90 and 7.26 (ABq 4H), 6.92 (s, 1H), 7.03 (s, 1H) and 7.48 (s, 1H).

EXAMPLE 8

Neopentyl 6-[2-(1H-imidazol-1-yl)-1-[[(4-methoxyphenyl)methoxy]methyl]ethoxy]hexanoate (a) Neopentyl 6-bromohexanoate A solution of 6-bromohexanoyl chloride (10.0 g, 0.047 mol) and 2,2-dimethylpropanol (4.96 g, 0.056 mol) in benzene (100 ml) was heated under reflux for 2 hours. The solvent was evaporated off under reduced pressure and the residue was dissolved in dichloromethane (200 ml), washed with aqueous sodium hydroxide (2M, 50 ml), water (50 ml) and dried (Na₂SO₄). The solvent was evaporated off under reduced pressure to give the crude product which was further purified by column chromatography (alumina, dichloromethane) to give neopentyl 6-bromohexanoate as a colourless oil.

¹H-NMR (δ-CDCl₃): 0.96 (s, 9H), 1.42–1.59 (m, 2H), 1.60–1.77 (m, 2H), 1.81–2.00 (m, 2H), 2.36 (t, 2H), 3.39 (t, 2H) and 3.78 (s, 2H).

(b) Neopentyl 6-[2-(1H-imidazol-1-yl)-1-[[(4-methoxyphenyl)methoxy]methyl]ethoxy]hexanoate This compound was prepared as in Example 7b using neopentyl 6-bromohexanoate. The crude product was purified by column chromatography (silica gel, 5% ethanol in chloroform) to give the title product as a pale-yellow oil.

¹H-NMR (δ-CDCl₃): 0.93 (s, 9H), 1.22–1.70 (m, 6H), 2.32 (t, 2H), 3.21–3.50 (m, 4H), 3.59 (m, 1H), 3.76 (s, 2H), 3.80 (s, 3H), 3.94–4.18 (m, 2H), 4.45 (s, 2H), 6.90 and 7.26 (ABq, 4H), 6.92 (s, 1H), 7.02 (s, 1H) and 7.46 (s, 1H).

EXAMPLE 9

2,2-Dimethyl-6-[2-(1H-imidazol-1-yl)-1-[[(4-methoxyphenyl)methoxy]methyl]ethoxy]hexanoic acid (a) Ethyl 2,2-dimethyl-6-bromohexanoate A solution of n-butyllithium (1.6M, 63 ml, 0.10 mol.) in hexane was added dropwise to a solution of diisopropylamine (10.1 g, 0.10 mol.) in anhydrous tetrahydrofuran (100 ml) at −50° C. The mixture was stirred for 0.5 hours and cooled to −70° C. A solution of ethyl isobutyrate (12.2 g, 0.105 mol.) in tetrahydrofuran (20 ml) was then added and the resulting mixture was stirred at −70° C. for 1 hour. 1,4-Dibromobutane (30.4 g, 0.14 mol) was then added, followed by hexamethylphosphoramide (30 g). The mixture was maintained at −70° C. for 0.5 hours and then warmed to room temperature over 1 hour. The solvent was evaporated off under reduced pressure, treated with an excess of an aqueous saturated solution of ammonium chloride (500 ml) and extracted with ethyl acetate (2×150 ml). The combined extracts were washed with water (100 ml), hydrochloric acid (1N, 2×100 ml) aqueous saturated sodium hydrogen carbonate solution (100 ml) and dried (MgSO₄). The solvent was evaporated off under reduced pressure and the residue was distilled to give ethyl 2,2-dimethyl-6-bromohexanoate as a pale yellow oil, (b.p. 73° C., 0.06 mm Hg).

¹H-NMR(δ-CDCl₃): 1.20 (s, 6H), 1.28 (t, 3H), 1.35–1.62 (m, 4H), 1.78–2.00 (quintet, 2H), 3.42 (t, 2H) and 4.15 (q, 2H).

(b) 2,2-Dimethyl-6-[2-(1H-imidazol-1-yl)-1-[[(4-methoxyphenyl)methoxy]methyl]ethoxy]hexanoic acid This compound was prepared by the method of Example 1c but using ethyl 2,2-dimethyl-6-bromohexanoate. The crude product ws purified by column chromatography (silica gel, 10% ethanol in chloroform) to give the title compound as a pale yellow oil.

¹H NMR (δ-CDCl₃): 1.20 (s, 6H), 1.15–1.60 (m, 6H), 3.15–3.37 (m, 2H), 3.37–3.65 (m, 3H), 3.83 (s, 3H), 3.90–4.20 (m, 2H), 4.45 (s, 2H), 6.90 (s, 1H), 6.91 and 7.25 (ABq, 4H), 7.04 (s, 1H), 7.65 (s, 1H) and 9.20 (br, s, 1H, D₂O exchangeable).

EXAMPLE 10

Ethyl 2,2-dimethyl-6-[2-(1H-imidazol-1-yl)-1-[[(4-methoxyphenyl)methoxy]methyl]ethoxy]hexanoate This compound was prepared as described in Example 4 but using 2,2-dimethyl-6-[2-(1H-imidazol-1-yl)-1-[[(4-methoxyphenyl)methoxy]ethoxy]hexanoic acid (Example 9). The crude product was purified by column chromatography (silica gel, 10% ethanol in chloroform) to give the title compound as a colourless oil.

¹H-NMR (δ-CDCl₃): 1.15 (s, 6H), 1.25 (t, 3H), 1.37–1.55 (m, 6H), 3.20–3.35 (m, 2H), 3.40–3.65 (m, 3H), 3.80 (s, 3H), 3.90–4.20 (m, 4H), 4.45 (s, 2H), 6.90 (d, 2H), 6.93 (s, 1H), 7.00 (s, 1H), 7.25 (d, 2H), and 7.45 (s, 1H).

EXAMPLE 11

1-[2-Methoxy-3-[(4-methoxyphenyl)methoxy]propyl]-1H-imidazole

A solution of 1-[2-hydroxy-3-[(4-methoxyphenyl)methoxy]propyl]]-1H-imidazole (20 g, 0.0763 mol, prepared by the method of Example 1a,b), in dry tetrahydrofuran (300 ml) was added dropwise to a stirred slurry of sodium hydride (3.32 g of a 60% dispersion in oil, 0.083 mol) and stirred for 5 hours at 25° C. A solu- NMR (δ-CDCl₃): 3.32 (s, 3H), 3.37 (m, 2H), 3.51 (m, 1H), 3.79 (s, 3H), 4.06 (m, 2H), 4.44 (s, 2H) and 6.70–7.45 (m, 7H).

TABLE 1

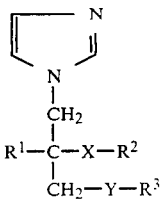

The compounds of Examples 12 to 18 in the following Table were prepared as for Example 11 by reacting the compound prepared according to Example (1a,b) with a compound of formula

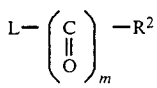

where L, m, R¹, R¹, R³, X and Y are as hereinbefore defined and are specifically represented within the Table.

| Ex No. | m | L | X | Y | R² | R³ | NMR (δ-CDCl₃) |
|---|---|---|---|---|---|---|---|
| 12 | 0 | OCH₃ | O | O | CH₂CH₂CH₂CH₂CH₂Cl | —CH₂—⟨C₆H₄⟩—OCH₃ | 1.15–1.55 (6H,m), 3.05–3.70 (7H,m), 3.79 (3H,s), 4.04 (2H,t), 4.44 (2H,s), 6.82–7.30 (6H,m), 7.45 (1H,s). |
| 13 | 0 | I | O | O | —CH₂CH₃ | —CH₂—⟨C₆H₄⟩—OCH₃ | 1.11 (3H,t), 3.15–3.70 (5H,m), 3.80 (3H,s), 4.05 (2H,t), 4.44 (2H,s), 6.82–7.30 (6H,m), 7.47 (1H,s). |
| 14 | 0 | I | O | O | —CH₂CH₂CH₂CH₃ | —CH₂—⟨C₆H₄⟩—OCH₃ | 0.88 (3H,t), 1.10–1.60 (4H,m), 3.10–3.70 (5H,m), 3.80 (3H,s), 4.05 (2H,t), 4.44 (2H,s), 6.82–7.30 (6H,m), 7.46 (1H,s). |
| 15 | 0 | I | O | O | —CH₂CH₂CH₂CH₂CH₃ | —CH₂—⟨C₆H₄⟩—OCH₃ | 0.87 (3H,t), 1.12–1.60 (6H,m), 3.15–3.60 (5H,m), 3.79 (3H,s), 4.06 (2H,m), 4.44 (2H,s), 6.82–7.30 (6H,m), 7.40 (1H,s). |
| 16 | 0 | Br | O | O | CH₂C≡CH | —CH₂—⟨C₆H₄⟩—OCH₃ | 2.35 (1H,t), 3.15–3.55 (3H,m), 3.60–3.90 (2H,m), 3.76 (3H,s), 4.00–4.15 (4H,m), 4.40 (2H,s), 6.78–7.30 (6H,m), 7.40 (1H,s). |
| 17 | 0 | Br | O | O | CH₂CH=CH₂ | —CH₂—⟨C₆H₄⟩—OCH₃ | 3.10–3.40 (2H,m), 3.60 (1H,m), 3.81 (3H,s), 3.40 (2H,m), 4.08 (2H,m), 4.44 (2H,s), 4.95–5.30 (2H,m), 5.45–6.00 (1H,m), and 6.65–7.45 (7H,m). |
| 18 | 1 | Cl | O | O | CH₃ | —CH₂—⟨C₆H₄⟩—OCH₃ | 2.04 (3H,s), 3.35–3.45 (2H,dd), 3.81 (3H,s), 4.15–4.22 (2H,d), 4.45 (2H,s), 5.10 (1H,br.t) and 6.70–7.45 (7H,m). | tion of methyl iodide (12 g, 0.0845 mol) in dry tetrahydrofuran (50 cm³) was then added dropwise and the resulting mixture was stirred at room temperature for 10 hours. The solution was filtered and the solvent was evaporated off under reduced pressure to give an oil which was purified by column chromatography (silica gel, 10% hexane in t-butylmethyl ether to 5% methanol in t-butylmethyl ether) to give the product as a colourless oil.

EXAMPLE 19

Ethyl 6-[2-(1H-imidazol-1-yl)-1-[[(4-methoxyphenyl)methoxy]methyl]ethoxy]-5-oxopentanoate A solution of ethyl 4-(chloroformyl)butyrate (3.4 g, 0.019 mol) in dichloromethane (20 ml) was added dropwise over 0.3 hours to a stirred solution of 1-[2-hydroxy-3-[(4-methoxyphenyl)methoxy]propyl]-1H-imidazole (Example 1b, 5.0 g, 0.019 mol) and triethylamine (1.9 g, 0.019 mol) in dichloromethane (50 ml) at room temperature. The solution was stirred for 2 hours, washed with an aqueous saturated solution of sodium chloride and dried (MgSO$_4$). The solvent was evaporated off under reduced pressure to give the crude product which was purified by column chromatography (silica gel, 2% ethanol in chloroform) to give ethyl 6-[2-(1H-imidazol-1-yl)-1-[[(4-methoxyphenyl)methoxy]methyl]-ethoxy]-5-oxopentanoate as a pale yellow oil.

$^1$H-NMR ($\delta$-CDCl$_3$): 1.25 (t, 3H), 1.90 (quintet, 2H), 2.32 (t, 2H), 2.37 (t, 2H), 3.32–3.54 (m, 2H), 3.81 (s, 3H), 4.14 (q, 2H), 4.20 (d, 2H), 4.44 (ABq, 2H), 5.15 (quintet, 1H), 6.88 (s, 1H), 6.90 and 7.25 (ABq, 4H), 7.03 (s, 1H), and 7.43 (s, 1H).

Examples 20–26 were prepared either from Example 1 by standard modifications of the carboxyl group or from Example 4 by standard modifications of the carboxyethyl group as described in detail below.

EXAMPLE 20

6-[2-(1H-Imidazol-1-yl)-1-[[(4-methoxyphenyl)methoxy]methyl]ethoxy]hexanamide

A stirred solution of 6-[2-(1H-imidazol-1-yl)-1-[[(4-methoxyphenyl)methoxy]methyl]ethoxy]hexanoic acid (Example 1; 10 g, 0.027M) and triethylamine (3.0 g, 0.030 mol) in dry dichloromethane (100 ml) at −50° C. was treated dropwise with ethyl chloroformate (3.2 g, 0.029 mol). The solution was allowed to warm up to 0° C. over 0.5 hours, cooled back to −78° C. and treated with gaseous ammonia. The solution was allowed to warm up to room temperature over 6 hours and washed with an aqueous saturated solution of sodium hydrogen carbonate and dried (Na$_2$CO$_3$). The solvent was evaporated off under reduced pressure to give a residue which was purified by column chromatography (silica gel, ethyl acetate to 10% methanol in ethyl acetate) to give 6-[2-(1H-imidazol-1-yl)-1-[[(4-methoxyphenyl)methoxy]methyl]-ethoxy]hexanamide as a pale yellow oil.

$^1$H-NMR ($\delta$-CDCl$_3$): 1.15–1.37 (m, 2H), 1.40–1.65 (m, 4H), 2.17 (t, 2H), 3.17–3.65 (m, 5H), 3.84 (s, 3H), 3.95–4.15 (m, 2H), 4.51 (ABq, 2H), 5.8 (broad s, 1H), 6.4 (broad s, 1H), 6.93 and 7.27 (ABq, 4H), 6.89 (s, 1H), 7.08 (s, 1H), and 7.53 (s, 1H).

EXAMPLE 21

N,N-Dimethyl-6-[2-(1H-imidazol-1-yl)-1-[[(4-methoxyphenyl)methoxy]methyl]ethoxy]hexanamide This compound was prepared as described in Example 20 using dimethylamine in place of ammonia. The crude product was purified by column chromatography (silica gel, ethyl acetate to 5% methanol in ethyl acetate) to give the title compound as a pale-yellow oil.

$^1$H-NMR ($\delta$-CDCl$_3$): 1.21–1.39 (m, 2H), 1.41–1.68 (m, 4H), 2.28 (t, 2H, 2.92 (s, 3H), 2.99 (s, 3H), 3.22–3.64 (m, 5H), 3.80 (s, 3H), 3.93–4.21 (m, 2H), 4.45 (s, 2H), 6.88 and 7.24 (ABq, 4H), 6.90 (s, 1H), 7.00 (s, 1H) and 7.48 (s, 1H).

EXAMPLE 22

1-[2-[(6-aminohexyl)oxy]-3-[(4-methoxyphenyl)methoxy]propyl]-1H-imidazole

6-[2-(1H-Imidazol-1-yl)-1[[(4-methoxyphenyl)methoxy]methyl]ethoxy]hexanamide (Example 20, 0.3 g, 0.0008 mol) in dry tetrahydrofuran (2 ml) was added to a stirred suspension of lithium aluminium hydride (0.5 g, 0.013 mol) in dry tetrahydrofuran (10 ml) under a nitrogen atmosphere. The resulting suspension was stirred under reflux for 24 hours cooled to room temperature and the residual lithium aluminium hydride destroyed using ethyl acetate (15 ml) followed by dilute sodium hydroxide solution (2N, 20 ml), the resulting solution was filtered and the filter cake was washed with ethyl acetate (50 ml), the organic layer was separated, dried (MgSO$_4$) and evaporated to an oil which was purified by column chromatography (silica gel, ethylacetate to 10% methanol in ethyl acetate) to yield the title compound as an oil.

$^1$H-NMR ($\delta$-CDCl$_3$): 1.2–1.35 (m, 4H), 1.4–1.6 (m, 4H), 2.3–2.6 (br. s, 2H), 3.4–3.6 (m, 3H), 3.6–3.8 (4H), 3.8 (s, 3H), 4.0–4.2 (m, 2H), 4.5 (s, 2H), 6.85 and 7.20 (ABq, 4H), 6.85 (s, 1H), 7.1 (s, 1H) and 7.5 (s, 1H).

EXAMPLE 23

1-[2-[(6-Hydroxyhexyl)oxy]-3-[(4-methoxyphenyl)methoxy]propyl]-1H-imidazole

A solution of ethyl 6-[2-(1H-imidazol-1-yl)-1-[[(4-methoxyphenyl)methoxy]methyl]ethoxy]hexanoate (Example 4; 10 g, 0.025 mol) in anhydrous tetrahydrofuran (50 ml) was added dropwise to a stirred slurry of lithium aluminium hydride (1.8 g, 0.047 mol) in anhydrous tetrahydrofuran (20 ml) under a nitrogen atmosphere. When the addition was complete the suspension was heated under reflux for 1 hour. Aqueous sodium hydroxide (2M, 2 ml) was added and the mixture was poured into an aqueous saturated solution of ammonium chloride (1000 ml) and extracted with dichloromethane. The combined extracts were dried (Na$_2$SO$_4$) and the solvent was evaporated off under reduced pressure to give the crude product which was purified by column chromatography (silica gel, ethyl acetate to 10% ethanol in ethyl acetate) to give 1-[2-[(6-hydroxyhexyl)oxy]-3-[(4-methoxyphenyl)methoxy]-propyl]-1H-imidazole as a pale yellow oil.

$^1$H-NMR ($\delta$-CDCl$_3$): 1.10–1.36 (m, 4H), 1.40–1.60 (m, 4H), 2.43 (broad s, 1H), 3.18–3.35 (m, 2H), 3.42–3.67 (m, 5H), 3.83 (s, 3H), 3.95–4.14 (m, 2H), 4.48 (ABq, 2H), 6.94 and 7.26 (ABq, 4H), 6.94 (s, 1H), 7.09 (s, 1H), and 7.52 (s, 1H).

EXAMPLE 24

1-[2-[(6-Methoxyhexyl)oxy]-3-[(4-methoxyphenyl)methoxy]propyl]-1H-imidazole

1-[2-[(6-Hydroxyhexyl)oxy]-3-[(4-methoxyphenyl)-methoxy]propyl]-1H-imidazole (Example 23) (0.3 g, 0.00086 mol) was added to a suspension of sodium hydride (0.006 g of an 80% dispersion in oil, 0.002 mol) in dry tetrahydrofuran (5 ml) at 25° C. and the resulting slurry stirred for 1 hour at this temperature. Methyl iodide (0.284 g, 0.002 mol) was then added and the resulting suspension stirred at 25° C. overnight. The suspension was then evaporated under reduced pressure and the residue poured into dilute hydrochloric acid (6N, 20 ml) and washed with ethyl acetate (2×5 ml), the aqueous phase was then basified with solid potassium carbonate and the liberated oil extracted into ethyl acetate (10 ml), the organic phase was then dried and evaporated under reduced pressure to give the product which was purified by column chromatography (silica gel, 10% methanol in ethyl acetate) to give the title compound as a pale yellow oil.

$^1$H-NMR ($\delta$-CDCl$_3$): 1.2–1.4 (m, 4H), 1.5–1.7 (m, 4H), 3.0–3.2 (m, 2H), 3.3 (s, 3H), 3.4–3.7 (m, 4H), 3.8 (s, 3H), 3.9–4.2 (m, 3H), 4.5 (s, 2H), 6.91 and 7.28 (ABq, 4H), 6.9 (s, 1H), 7.0 (s, 1H), and 7.7 (s, 1H).

EXAMPLE 25

6-[2-(1H-Imidazol-1-yl)-1-[(4-methoxyphenyl)methoxy]methyl]ethoxy]hexanal

1-[2-[(6-Hydroxyhexyl)oxy]-3-[(4-methoxyphenyl)-methoxy]propyl]-1H-imidazole (0.5 g, 0.0014 mol) was added as a solution in dichloromethane (10 ml) to a cool (−50° C.) solution of dimethyl sulfoxide (0.22 g, 0.0028 mol) containing trifluoroacetic anhydride (0.44 g, 0.0021 mol) in dichloromethane (20 ml) (the latter solution was prepared at −50° C. by slow addition of trifluoroacetic anhydride to a solution of dimethylsulfoxide in dichloromethane). After stirring the solution for 0.5 hours at −50° C., triethylamine (5.6 ml, 0.055 mol) was added over 10 min and the resulting solution was allowed to reach 25° C. over 0.75 hours. The solution was then poured into saturated aqueous sodium bicarbonate solution (50 ml) and the organic layer separated, dried and evaporated under reduced pressure, the resulting oil was purified (x2) by column chromatography (silica gel, chloroform to 10% methanol in chloroform) to yield the title compound as an oily solid.

$^1$H-NMR (δ-CDCl$_3$): 1.2–1.4 (m, 2H), 1.45–1.7 (m, 4H), 2.4 (t, 2H), 3.1–3.2 (m, 2H), 3.3–3.6 (m, 3H), 3.81 (s, 3H), 3.95–4.2 (m, 2H), 4.5 (s, 2H), 6.88 (s, 1H), 7.05 (s, 1H), 7.7 (s, 1H) and 9.7 (s, 1H).

EXAMPLE 26

Ethyl 6-[2-hydroxy-1-(1H-imidazol-1-yl methyl)ethoxy]hexanoate

A solution of ethyl 6-[2-(1H-imidazol-1-yl)-1-[[(4-methoxyphenyl)methoxy]methyl]ethoxy]hexanoate (Example 4; 5.8 g 0.014 mol) in ethanol (20 ml) and trifluoroacetic acid (1 ml) containing a catalytic amount of 10% palladium on carbon (0.5 g) was stirred at room temperature under a hydrogen atmosphere. When hydrogen uptake had ceased the solution was filtered and the solvent was evaporated off under reduced pressure. The residue was treated with a saturated aqueous solution of sodium hydrogen carbonate and extracted with dichloromethane. The extracts were dried (Na$_2$SO$_4$) and the solvent was evaporated off under reduced pressure to give the crude product which was purified by column chromatography (silica gel, chloroform to 5% ethanol in chloroform) to give ethyl 6-[2-hydroxy-1-(1H-imidazol-1-yl methyl)ethoxy]hexanoate as a pale yellow oil.

$^1$H-NMR (δ-CDCl$_3$): 1.34 (t, 3H), 1.30–1.50 (m, 2H), 1.50–1.78 (m, 4H), 2.38 (t, 2H), 3.00 (br.s, 1H, D$_2$O exchangeable), 3.36–3.50 (m, 1H), 3.50–3.76 (m, 4H), 4.00–4.30 (m, 4H), 6.98 (s, 1H), 7.08 (s, 1H) and 7.54 (s, 1H).

EXAMPLE 27

Ethyl 6-[2-(1H-imidazol-1-yl)-1-[[(4-bromophenyl)methoxy]methyl]ethoxy]hexanoate (a) 2,3-Epoxypropyl-4-bromobenzyl ether This compound was prepared as in Example 1a but using 4-bromobenzyl alcohol. The crude product was purified by column chromatography (silica gel, dichloromethane) to give 2,3-epoxyproyl-4-bromobenzyl ether as a colourless oil.

$^1$H-NMR (δ-CDCl$_3$): 2.55–2.64 (m, 1H), 2.74–2.84 (t, 1H), 3.12–3.24 (m, 1H), 3.34–3.46 (dd, 1H), 3.73–3.84 (dd, 1H), 4.44–4.60 (ABq, 2H), and 7.20 and 7.45 (ABq, 4H).

(b) 1-[2-Hydroxy-3-[(4-bromophenyl)methoxy]propyl]-1H-imidazole

This compound was prepared as in Example 1b but using 2,3-epoxypropyl-4-bromobenzyl ether. The crude product was recrystallised from dichloromethane/diethyl ether to give 1-[2-hydroxy-3-[(4-bromophenyl)-methoxy]propyl]-1H-imidazole as a colourless crystalline solid, m.p. 98°–100° C.

(c) Ethyl 6-[2-(1H-Imidazol-1-yl)-1-[[(4-bromophenyl)methoxy]-methyl]ethoxy]hexanoate This compound was prepared as in Example 1c but using 1-[2-hydroxy-3-[(4-bromophenyl)methoxy]propyl-1H-imidazole. The crude acid so obtained was converted directly into the title ester by the method of Example 4. The product so obtained was isolated by column chromatography (silica gel, chloroform) to give a colourless oil.

$^1$H-NMR (δ-CDCl$_3$): 1.26 (t, 3H), 1.28–1.40 (m, 2H), 1.46–1.68 (m, 4H), 2.28 (t, 2H), 3.24–3.50 (m, 2H), 3.61 (m, 1H), 3.94–4.20 (m, 4H), 4.46 (s, 2H), 6.92 (s, 1H), 7.02 (s, 1H), 7.20 and 7.46 (ABq, 4H), and 7.47 (s, 1H).

EXAMPLE 28

6-[2-(1H-Imidazolyl-1-yl)-1-[(phenylmethoxy)methyl]ethoxy]ethoxy]hexanoic acid (a) 2,3-Epoxypropyl benzyl ether This compound was prepared as in Example 1a but using benzyl alcohol. The product was used without purification for Example 27b.

(b) 1-[2-Hydroxy-3-[phenylmethoxy]propyl]-1H-imidazole

This compound was prepared as in Example 1b but using 2,3-epoxypropyl benzyl ether. The crude product was purified by column chromatography (silica gel, chloroform) to give 1-[2-hydroxy-3-[phenylmethoxy]-propyl]-1H-imidazole as a colourless oil.

(c) 6-[2-(1H-Imidazol-1-yl)-1-[(phenylmethoxy)methylethoxy]hexanoic acid

This compound was prepared as in Example 1c but using 1-[2-hydroxy-3-[phenylmethoxy]propyl]-1H-imidazole. The crude product was purified by column chromatography (silica gel, 20% methanol in ethyl acetate) to give the title compound as a pale yellow oil.

$^1$H-NMR (δ-CDCl$_3$): 1.2–1.4 (m, 2H), 1.5–1.7 (m, 4H), 2.3 (t, 2H), 3.2–3.4 (m, 2H), 3.5–3.7 (m, 3H), 4.0–4.2 (m, 2H), 4.5 (s, 2H), 6.95 (s, 1H), 7.1 (s, 1H), 7.3–7.4 (m, 5H), 7.76 (s, 1H) and 8.0 (br.s, 1H).

EXAMPLE 29

Ethyl 6-[2-(2H-imidazol-1-yl)-1-[(pentoxy)methyl]ethoxy]-hexanoate (a) 2,3-Epoxypropyl pentyl ether This compound was prepared as in Example 1a but using pentanol. The crude product was purified by column chromatography (silica gel, dichloromethane)

to give the 2,3-epoxypropyl pentyl ether as a yellow oil which was used without further purification.

(b) 1-[2-Hydroxy-3-(pentoxy)propyl]-1H-imidazole

This compound was prepared as in Example 1b but using 2,3-epoxypropyl pentyl ether. The crude product was purified by column chromatography (silica gel, chloroform) to give 1-[2-hydroxy-3-(pentoxy)propyl]-1H-imidazole as a yellow oil.

$^1$H-NMR ($\delta$-CDCl$_3$): 0.94 (m, 3H), 1.28–1.40 (m, 4H), 1.57 (m, 2H), 3.19–3.46 (m, 4H), 3.84–4.18 (m, 3H), 5.17 (brs, 1H) 6.84 (s, 1H), 6.92 (s, 1H) and 7.40 (s, 1H).

(c) Ethyl 6-[2-(1H-imidazol-1-yl)-1-[(pentoxy)methyl]ethoxy]-hexanoate

This compound was prepared as in Example 1c but using 1-[2-hydroxy-3-(pentoxy)propyl]-1H-imidazole. The crude acid as obtained was converted directly into its corresponding ethyl ester by the method of Example 4. The product was isolated by column chromatography (silica gel, chloroform) to give a pale yellow oil.

$^1$H-NMR ($\delta$-CDCl$_3$): 0.90 (m, 3H), 1.25 (t, 3H), 1.27–1.44 (m, 6H), 1.46–1.70 (m, 6H), 3.17–3.64 (m, 7H), 3.92–4.21 (m, 4H), 6.94 (s, 1H), 7.04 (s, 1H), 7.49 (s, 1H).

EXAMPLE 30

1-[2-[(4-Methoxyphenyl)methoxy]-3-(pentoxy)propyl]-1H-imidazole

1-[2-Hydroxy-3-(pentoxy)propyl]-1H-imidazole (Example 29b; 2.12 g, 0.01 mol) was added to a stirred suspension of powdered potassium hydroxide (2.24 g, 0.040 mol) in dimethylsulphoxide (10 ml) at 18° C. and stirred for 0.5 hours. 4-Methoxybenzyl chloride was then added and stirring was continued for 2 hours. Ethyl acetate (350 ml) was added and the solution was washed with water and dried (MgSO$_4$). Ths solvent was evaporated off under reduced pressure and the crude product was purified by column chromatography (silica gel, chloroform) to give 1-[2-[(4-methoxyphenyl)methoxy]-3-(pentoxy)propyl]-1H-imidazole as a pale-yellow oil.

$^1$H-NMR ($\delta$-CDCl$_3$): 0.91 (m, 3H), 1.28–1.40 (m, 4H), 1.60 (m, 2H), 3.21–3.52 (m, 4H), 3.72 (m, 1H), 3.80 (s, 3H), 3.96–4.19 (m, 2H), 4.34–4.52 (m, 2H), 6.86 and 7.14 (ABq, 4H), 6.94 (s, 1H), 7.06 (s, 1H) and 7.50 (s, 1H).

EXAMPLE 31

Ethyl 4-[[1-(1H-imidazol-1-yl methyl)-2-(pentoxy)ethoxy]methyl]benzoate

A solution of 1-[2-hydroxy-3-(pentoxy)propyl]-1H-imidazole (Example 29b, 2.12 g, 0.010 mol) in anhydrous tetrahydrofuran (15 ml) was treated with sodium hydride, 0.44 g of a 60% dispersion in oil, 0.011 mol) and stirred at room temperature for 1 hour. Ethyl 4-(bromomethyl)benzoate (2.67 g, 0.011 mol) was then added and the mixture was stirred at room temperature for 12 hours. The solvent was evaporated off under reduced pressure and the residue was dissolved in ethyl acetate, washed with water and dried (MgSO$_4$). The solvent was evaporated off under reduced pressure and the crude product was purified by column chromatography (silica gel, chloroform) to give ethyl 4-[[1-(1H-imidazol-1-ylmethyl)-2-(pentoxy)ethoxy]methyl]benzoate as a yellow oil.

$^1$H-NMR ($\delta$-CDCl$_3$): 0.91 (m, 3H), 1.24–1.47 (m, 7H), 1.73–1.79 (m, 2H), 3.28–3.53 (m, 4H), 3.76 (m, 1H), 4.01–4.25 (m, 2H), 4.39 (q, 2H), 4.47–4.69 (m, 2H), 6.95 (s, 1H), 7.07 (s, 1H), 7.28 and 8.00 (ABq, 4H) and 7.51 (s, 1H).

EXAMPLE 32

Ethyl 6-[[2-(1H-imidazol-1-yl)-1-[[(4-methoxyphenyl)methoxy]methyl]ethyl]amino]hexanoate (a) $\alpha$-[[(4-Methoxyphenyl)methoxy]methyl]-1H-imidazole-1-ethanol,4-methylbenzenesulphonate 4-Toluene sulphonyl chloride (18.0 g, 0.094 mol) was added in portions to a stirred solution of 1-[2-hydroxy-3-[(4-methoxy-phenyl)methoxy]propyl]-1H-imidazole (Example 1b; 31.4 g, 0.12 mol) in dry pyridine (100 ml)/dimethoxyethane (60 ml) at 0° C. over 0.5 hours. The solution was stirred at 0° C. for 4 hours. The reaction mixture was poured into ethyl acetate (1200 ml), washed with water (4×200 ml), was dried (MgSO$_4$). The solvent was evaporated off under reduced pressure to give the crude product as a yellow oil which was further purified by chromatography (silica gel, 10% ethanol in chloroform) to give $\alpha$-[[(4-Methoxyphenyl)-methoxy)methyl]-1H-imidazole-1-ethanol,4-methylbenzenesulphonate as a colourless crystalline solid m.p. 130°–131° C. (ether-ethanol).

$^1$H-NMR ($\delta$-CDCl$_3$): 2.40 (s, 3H), 3.31–3.50 (m, 2H), 3.80 (m, 3H), 4.12–4.29 (m, 2H), 4.32–4.44 (m, 2H), 4.68 (m, 1H), 6.76 (s, 1H), 6.88 and 7.18 (ABq, 4H), 6.94 (s, 1H), 7.26 and 7.66 (ABq, 4H), and 7.32 (s, 1H).

(b) 1-[2-Azido-3-[(4-methoxyphenyl)methoxy]propyl]1H-imidazole

A solution of $\alpha$-[[(4-methoxyphenyl)methoxy]methyl]-1H-imidazole-1-ethanol,4-methylbenzenesulphonate (6.39 g, 0.015M) in dry dimethylformamide (30 ml) was treated with sodium azide (1.69 g, 0.0225M) and heated at 70° C. for 16 hours. The solvent was evaporated off under reduced pressure and the residue was dissolved in ethyl acetate, washed with water and dried (MgSO$_4$). The solvent was evaporated off under reduced pressure to give the crude product which was further purified by column chromatography (silica gel, 10% ethanol in chloroform) to give 1-[2-azido-3-[(4-methoxyphenyl)methoxy]propyl]-1H-imidazole as a pale yellow oil.

$^1$H-NMR ($\delta$-CDCl$_3$): 3.45 (m, 2H), 3.60 (m, 1H), 3.75 (s, 3H), 4.00 (m, 2H), 4.45 (s, 2H) and 6.70–7.45 (m, 7H).

(c) 1-[2-Amino-3-[(4-methoxyphenyl)methoxy]propyl]-1H-imidazole

A solution of 1-[2-azido-3-[(4-methoxyphenyl)methoxy]propyl]-1H-imidazole (5.1 g, 0.018 mol) in dry tetrahydrofuran (10 ml) was added dropwise to a stirred slurry of lithium aluminium hydride (0.68 g, 0.018 mol) in dry tetrahydrofuran (40 ml) at room temperature under a stream of dry nitrogen. When the addition was complete the reaction mixture was heated under reflux for 18 hours. The solvent was evaporated off under reduced pressure and the residue was extracted with ethyl acetate, washed with saturated aqueous ammonium chloride solution and dried (MgSO$_4$). The solvent was evaporated off under reduced pressure to give 1-[2-amino-3-[(4-methoxyphenyl)methoxy]propyl]-1H- imidazole as an oil which was used directly without further purification.

$^1$H-NMR (δ-CDCl$_3$): 1.44 (br.s, 2H), 3.29 (br.s, 3H), 3.80 (s, 3H), 3.96 (m, 2H), 4.44 (s, 2H) and 6.60–7.45 (m, 7H).

(d) Ethyl 6-[[2-(1H-imidazol-1-yl)-1H-[[(4-methoxyphenylmethoxy]methyl]ethyl]amino]hexanoate A mixture of 1-[2-amino-3-[(4-methoxyphenyl)methoxy]propyl]-1H-imidazole (2.0 g, 0.0077 mol), ethyl 6-bromohexanoate (1.71 g, 0.0077 mol), anhydrous potassium carbonate (2.12 g, 0.015 mol) and potassium iodide (0.1 g, 0.0006 mol) in anhydrous dimethylformamide was stirred at room temperature for 12 hours. The solvent was evaporated off under reduced pressure and the reside was dissolved in dichloromethane, washed with water and dried (Na$_2$SO$_4$). The solvent was evaporated off under reduced pressure to give the crude product which was purified by column chromatography (silica gel, chloroform to 10% ethanol in chloroform) to give ethyl 6-[[2-(1H-imidazol-1-yl)-1H-[[(4-methoxyphenyl)methoxy]methyl]ethyl]amino]hexanoate as a pale-yellow oil.

$^1$H-NMR (δ-CDCl$_3$): 1.24 (t, 3H), 1.24–1.66 (m, 7H), 2.27 (t, 2H), 2.40–2.66 (m, 2H), 2.98 (m, 1H), 3.18–3.36 (m, 2H), 3.80 (s, 3H), 4.00 (d, 2H), 4.12 (q, 2H), 4.41 (s, 2H), 6.89 and 7.23 (ABq, 4H), 6.87 (s, 1H), 7.03 (s, 1H) and 7.42 (s, 1H).

EXAMPLE 33

Ethyl 5-[[2-(1H-imidazol-1-yl)-1-[[(4-methoxyphenyl)methoxy]methyl]ethyl]amino]pentanoate This compound was prepared as described in Example 32b but using ethyl 5-bromopentanoate. The crude product was purified by column chromatography (silica gel, chloroform to 5% ethanol in chloroform) to give the title compound as a pale-yellow oil.

$^1$H-NMR (δ-CDCl$_3$): 1.25 (t, 3H), 1.38–1.70 (m, 4H), 1.77 (br.s, 1H), 2.29 (t, 2H), 2.48–2.68 (m, 2H), 2.98 (m, 1H), 3.21–3.36 (m, 2H), 3.80 (s, 3H), 4.01 (d, 2H), 4.12 (q, 2H), 4.43 (s, 2H), 6.89 and 7.25 (ABq, 4H), 6.92 (s, 1H), 7.02 (s, 1H) and 7.46 (s, 1H).

EXAMPLE 34

Ethyl 5-[[2-(1H-imidazol-1-yl)-1-[[(4-methoxyphenyl)methoxy]methyl]ethyl]amino]-5-oxopentanoate A solution of ethyl 4-(chloroformyl)butyrate (0.714 g, 0.004 mol) in dichloromethane (5 ml) was added dropwise to a stirred solution of 1-[2-amino-3-[(4-methoxyphenyl)methoxy]propyl]-1H-imidazole (Example 32c; 1.0 g, 0.0038 mol) and triethylamine (0.4 g, 0.004 mol) in dichloromethane (20 ml) at room temperature. The solution was stirred for 12 hours, washed with an aqueous saturated solution of ammonium chloride and dried (Na$_2$SO$_4$). The solvent was evaporated off under reduced pressure and the crude product was purified by column chromatography (silica gel, 2% ethanol in chloroform) to give ethyl 5-[[2-(1H-imidazol-1-yl)-1-[[(4-methoxyphenyl)methoxy]methyl]ethyl]amino]-5-oxopentanoate as a pale-yellow oil.

$^1$H-NMR (δ-CDCl$_3$): 1.26 (t, 3H), 1.97 (m, 2H), 2.26 (t, 2H), 2.37 (t, 2H), 3.36 (m, 2H), 3.82 (s, 3H), 4.05–4.20 (m, 4H), 4.33 (m, 1H), 4.46 (s, 2H), 6.57 (d, 1H), 6.87 (s, 1H), 6.90 and 6.25 (ABq, 4H), 6.99 (s, 1H) and 7.37 (s, 1H).

EXAMPLE 35

6-[1-(1H-Imidazol-1-ylmethyl)-4-phenylbutoxy]hexanoic acid (a) 5-Phenylpent-1-ene A solution of phenethyl magnesium bromide (prepared from 25 1 g, 0.135 mol of phenethyl bromide and excess magnesium turnings) in anhydrous tetrahydrofuran (50 ml) was added to a stirred solution of allyl bromide (16.34 g, 0.135 mol) in anhydrous tetrahydrofuran (150 ml) at room temperature and under an atmosphere of dry nitrogen. The mixture was stirred at room temperature for 3 hours and the solvent was then evaporated off under reduced pressure and the residue was dissolved in ethyl acetate. The solution was washed with a saturated aqueous solution of ammonium chloride and the solvent was evaporated off under reduced pressure to give an oil which was distilled to give 5-phenylpent-1-ene as a colourless oil (b.p. 40° C., 0.5 mm, Hg).

$^1$H-NMR (δ-CDCl$_3$): 1.64–1.78 (m, 2H), 2.00–2.14 (m, 2H), 2.61 (t, 2H), 4.89–5.07 (m, 2H), 5.72–5.92 (m, 1H), and 7.09–7.31 (m, 5H).

(b) 2-(3-Phenylpropyl)oxirane

5-Phenylpent-1-ene (14.2 g, 0.0973 mol) and m-chloroperbenzoic acid (16.79 g, 0.0973 mol) in dichloromethane (300 ml) was stirred at room temperature for 4 hours. The solution was washed with saturated aqueous sodium hydrogen carbonate solution and dried (MgSO$_4$). The solvent was evaporated off under reduced pressure to give an oil which was distilled to give 2-(3-phenylpropyl)oxirane (b.p. 85° C., 0.4 mm.Hg).

$^1$H-NMR (δ-CDCl$_3$): 1.66–1.92 (m, 4H), 2.45 (m, 1H), 2.66 (t, 2H), 2.73 (t, 1H), 2.94 (m, 1H) and 7.10–7.32 (m, 5H).

(c) 1-[1-(2-Hydroxy-5-phenylpentyl)]-1H-imidazole

Imidazole (50.32 g, 0.74 mol) was added to a solution of 2-(3-phenylpropyl)oxirane (30 g, 0.185 mol) in acetonitrile (500 ml) and the mixture was heated under reflux for 7 hours. The solvent was evaporated off under reduced pressure and the residue was dissolved in ethyl acetate, washed with water and dried (MgSO$_4$). The solvent was evaporated off under reduced pressure to give the crude product which was recrystallised from dichloromethane/hexane to give 1-[1-(2-hydroxy-5-phenylpentyl)]-1H-imidazole as a colourless crystalline solid, m.p. 72°–74° C.

$^1$H-NMR (δ-CDCl$_3$): 1.42–1.57 (m, 2H), 1.63–1.99 (m, 2H), 2.66 (t, 2H), 3.70–3.96 (m, 3H), 4.62 (br.s, 1H), 6.81 (m, 2H) and 7.13–7.35 (m, 6H).

(d) 6-[1-(1H-Imidazol-1-ylmethyl)-4-phenylbutoxy]hexanoic acid

This compound was prepared as in Example 1c but using 1-[1-(2-hydroxy-5-phenylpentyl)]-1H-imidazole. The crude product was purified by column chromatography (silica gel, 10% ethanol in chloroform), to give the title compound as a colourless oil.

$^1$H-NMR (δ-CDCl$_3$): 1.26–1.86 (m, 10H), 2.34 (t, 2H), 2.62 (t, 2H), 3.10–3.24 (m, 1H), 3.26–3.49 (m, 2H), 3.78–4.04 (m, 2H), 6.94 (bs,s, 1H), 7.10 (br.s, 1H), 7.12–7.35 (m, 5H), 7.74 (br.s, 1H) and 10.96 (br.s, 1H).

EXAMPLE 36

Ethyl 6-[1-(1H-imidazol-1-ylmethyl)-4-phenylbutoxy]hexanoate

This compound was prepared as in example 4 but using 6-[1-(1H-imidazol-1-ylmethyl)-4-phenylbutoxy]hexanoic acid (Example 35d). The crude product was purified by column chromatography (silica gel, 3% ethanol in chloroform) to give the title compound as a pale yellow oil.

$^1$H-NMR ($\delta$-CDCl$_3$): 1.18–1.82 (m, 13H), 2.26 (t, 2H), 2.62 (t, 2H), 3.12–3.46 (m, 3H) 3.78–4.02 (m, 2H), 4.12 (q, 2H), 6.90 (s, 1H), 7.03 (s, 1H), 7.12–7.30 (m, 5H), and 7.46 (s, 1H).

EXAMPLE 37

1-[2-[(4-Methoxyphenyl)methoxy]-5-phenylpentyl]-1H-imidazole

This compound was prepared as in example 30 but using 1-[1-(2-hydroxy-5-phenylpentyl)]-1H-imidazole (Example 35c). The crude product was purified by column chromatography (silica gel, chloroform) to give the title compound as a pale yellow oil.

$^1$H-NMR ($\delta$-CDCl$_3$): 1.42–1.88 (m, 4H), 2.59 (t, 2H), 3.57 (m, 1H), 3.78 (s, 3H), 3.81–4.00 (m, 2H), 4.13–4.30 (m, 2H), 6.80–7.36 (m, 11H) and 7.46 (s, 1H).

EXAMPLE 38

6-[1-(1H-Imidazol-1-ylmethyl)-4-(4-methoxyphenyl)butoxy]hexanoic acid

(a) 5-(4-Methoxyphenyl)pent-1-ene

This compound was prepared as in Example 35a using 4-methoxyphenethyl magnesium bromide prepared from 4-methoxyphenethyl bromide and magnesium turnings. The crude oil isolated after work-up was distilled to give the title compound (b.p. 65° C., 0.3 mm.Hg), as a colourless oil.

$^1$H-NMR ($\delta$-CDCl$_3$): 1.68 (m, 2H), 2.07 (m, 2H), 2.55 (m, 2H), 3.70 (s, 3H), 4.90–5.10 (m, 2H), 5.70–5.90 (m, 1H), 6.81 and 7.06 (ABq, 4H).

(b) 2-[3-(4-Methoxyphenyl)propyl]oxirane

This compound was prepared as in Example 35b using 5-(4-methoxyphenyl)pent-1-ene. The compound was purified by column chromatography (silica gel, chloroform), to give a colourless oil.

$^1$H-NMR ($\delta$-CDCl$_3$): 1.40–1.80 (m, 4H), 2.40 (m, 1H), 2.58 (t, 2H), 2.68 (m, 1H), 2.86 (m, 1H), 3.70 (s, 3H), 6.81 and 7.06 (ABq, 4H).

(c) 1-[1-[2-Hydroxy-5-(4-methoxyphenyl)pentyl]]-1H-imidazole

This compound was prepared by the same procedure as in Example 35c using 2-[3-(4-methoxyphenyl)propyl]oxirane. Column chromatography (silica gel, 5% ethanol in chloroform) of the crude reaction mixture and subsequent recrystallisation from dichloromethane/pentane gave the title compound as a colourless crystalline solid (m.p. 90.5°–91.5° C.).

$^1$H-NMR ($\delta$-CDCl$_3$): 1.39–1.52 (m, 2H), 1.55–1.94 (m, 2H), 2.56 (t, 2H), 3.74 (s, 3H), 3.64–3.89 (m, 3H), 5.34 (br.s, 1H), 6.78 (s, 1H), 6.80 and 7.08 (ABq, 4H), 6.84 (s, 1H) and 7.24 (s, 1H).

(d) 6-[1-(1H-Imidazol-1-ylmethyl)-4-(4-methoxyphenyl)butoxy]hexanoic acid

This compound was prepared as in Example 1c but using 1-[1-[2-hydroxy-5-(4-methoxyphenyl)pentyl-1H-imidazole. Purification by column chromatography (silica gel, 10% ethanol/chloroform) gave the title compound as a colourless oil.

$^1$H-NMR ($\delta$-CDCl$_3$): 1.22–1.81 (m, 10H), 2.31 (t, 2H), 2.58 (t, 2H), 3.09–3.21 (m, 1H), 3.37–3.50 (m, 2H), 3.80 (s, 3H), 3.83–4.11 (m, 2H), 6.83 and 7.09 (ABq, 4H), 6.92 (s, 1H), 7.10 (s, 1H), 7.83 (s, 1H) and 9.71 (br.s, 1H).

EXAMPLE 39

Ethyl 6-[1-(1H-imidazol-1-ylmethyl)-4-(4-methoxyphenyl)butoxy]hexanoate

The compound was prepared as in Example 4 but using 1-[1-[2-hydroxy-5-(4-methoxyphenyl)pentyl]]-1H-imidazole (Example 38d). The product was isolated by column chromatography (silica gel, 5% ethanol in chloroform) as a colourless oil.

$^1$H-NMR ($\delta$-CDCl$_3$): 1.28 (t, 3H), 1.28–1.79 (m, 10H), 2.29 (t, 2H), 2.58 (t, 2H), 3.13–3.47 (m, 3H), 3.78 (s, 3H), 3.81–4.00 (m, 2H), 4.12 (q, 2H), 6.83 and 7.08 (ABq, 4H), 6.91 (s, 1H), 7.06 (s, 1H) and 7.60 (s, 1H).

EXAMPLE 40

1-[2-[(4-Methoxyphenyl)methoxy]-5-(4-methoxyphenyl)pentyl]-1H-imidazole

This compound was prepared as for Example 30 using 1-[1-[2-hydroxy-5-(4-methoxyphenyl)pentyl)]]-1H-imidazole (Example 38c). The product was isolated by column chromatography (silica gel, chloroform) as pale-yellow oil.

$^1$H-NMR ($\delta$-CDCl$_3$): 1.37–1.81 (m, 4H), 2.55 (t, 2H), 3.56 (m, 1H), 3.72 (s, 6H), 3.70–4.04 (m, 2H), 4.08–4.39 (m, 2H), 6.77–6.85 (m, 5H), 6.91 (s, 1H), 6.98–7.17 (m, 4H) and 7.51 (s, 1H).

EXAMPLE 41

Ethyl 4-[1-(1H-imidazol-1-ylmethyl)-4-(4-methoxyphenyl)butoxy]benzoate

This compound was prepared as for Example 31 using 1-[1-[2-hydroxy-5-(4-methoxyphenyl)pentyl]]-1H-imidazole (Example 38c). The pure product was isolated by column chromatography (silica gel, chloroform) as a pale yellow oil.

$^1$H-NMR ($\delta$-CDCl$_3$): 1.40 (t, 3H), 1.44–1.82 (m, 4H), 2.58 (t, 2H), 3.60 (m, 1H), 3.80 (s, 3H), 3.86–4.10 (m, 2H), 4.20–4.4 (m, 4H), 6.81 (s, 1H), 6.83 and 7.06 (ABq, 4H), 6.92 (s, 1H), 7.25 and 8.02 (ABq, 4H) and 7.52 (s, 1H).

EXAMPLE 42

6-[1-(1H-Imidazol-1-ylmethyl)nonoxy]hexanoic acid

(a) 1,2-Epoxydecane

Epoxidation of 1-decene according to the procedure of Example 35b gave the title compound as a colourless oil which was used without further purification.

$^1$H-NMR ($\delta$-CDCl$_3$): 0.89 (m, 3H), 1.21–1.73 (m, 14H), 2.44 (m, 1H), 2.72 (m, 1H), 2.88 (m, 1H).

(b) 1-[1-(2-Hydroxydecyl)]-1H-imidazole

This compound was prepared according to the method of Example 35c using 1,2-epoxydecane. The product was isolated by column chromatography (silica gel, 2–5% ethanol in chloroform) which gave a pale yellow oil which solidified on standing. Recrystallisation from diethyl ether gave the analytical sample (m.p. 59.5°–61° C.) as a colourless crystalline solid.

$^1$H-NMR ($\delta$-CDCl$_3$): 0.90 (m, 3H), 1.16–1.64 (m, 14H), 3.74–4.02 (m, 3H), 5.30 (br.s, 1H), 6.87 (s, 1H), 6.91 (s, 1H), 7.36 (s, 1H).

(c) 6-[1-(1H-Imidazol-1-ylmethyl)nonoxy]hexanoic acid

This compound was prepared according to the procedure of Example 1c from 1-[1-(2-hydroxydecyl)]-1H-imidazole. The product was isolated by column chromatography (silica gel, 5% ethanol in chloroform) as a colourless oil.

$^1$H-NMR ($\delta$-CDCl$_3$): 0.82–0.98 (m, 3H), 1.17–1.73 (m, 20H), 2.27–2.44 (m, 2H), 3.13–3.27 (m, 1H), 3.35–3.50 (m, 2H), 3.81–4.10 (m, 2H), 6.91–7.13 (br.s, 2H) and 7.77 (br.s, 1H).

EXAMPLE 43

Ethyl 6-(1H-imidazol-1-ylmethyl)nonoxy]hexanoate

This compound was prepared as in Example 4 but using 6-[1-(1H-imidazol-1-ylmethyl)nonoxy]hexanoic acid (Example 42c). The crude product was purified by column chromatography (silica gel, 3% ethanol in chloroform) to give the title compound as a colourless oil.

$^1$H-NMR ($\delta$-CDCl$_3$): 0.90 (m, 3H), 1.21–1.72, (m, 23H), 2.30 (t, 2H), 3.21 (m, 1H), 3.37–3.51 (m, 2H), 3.85–4.11 (m, 2H), 4.1 (q, 2H), 7.00 (s, 1H), 7.14 (s, 1H) and 7.83 (s, 1H).

EXAMPLE 44

Ethyl 6-[1-(1H-imidazol-1-ylmethyl)-4-phenylbutylthio]hexanoate

(a) 2-(3-Phenylpropyl)thiirane

To a stirred solution of 2-(3-phenylpropyl)oxirane (Example 35b) (2.0 g, 0.0123 mol) and triphenylphosphine sulphide (3.62 g, 0.0123 mol) in toluene (20 ml), trifluoroacetic acid (1.40 g, 0.0123 mol) was added over 5 min. After stirring for 1 hour at room temperature, the reaction mixture was washed with water, sodium hydrogen carbonate solution and again with water. After drying (MgSO$_4$) and removal of solvent at reduced pressure, the product contaminated with triphenylphosphine oxide was isolated as a crystalline mass. Attempted purification of the thiirane resulted in its extensive decomposition and it was therefore used in its crude state.

$^1$H-NMR ($\delta$-CDCl$_3$): 1.74–1.97 (m, 4H), 2.12 (m, 1H), 2.47 (m, 1H), 2.66 (t, 2H), 2.87 (m, 1H) an 7.09–7.37 (m, 5H).

(b) 1-[1-(2-Mercapto-5-phenylpentyl)]-1H-imidazole

This compound was prepared according to the procedure of Example 35c using 2-(3-phenylpropyl)thiirane. The crude reaction mixture after removal of acetonitrile was dissolved in ethyl acetate, washed with water, and then extracted with 1N hydrochloric acid. The combined acid extracts were basified using 1N sodium hydroxide solution and extracted with dichloromethane. The combined organic extracts were dried (MgSO$_4$) and the solvent removed at reduced pressure. The product was isolated by column chromatography (silica gel, chloroform) as a colourless oil.

$^1$H-NMR ($\delta$-CDCl$_3$): 1.34 (d, 1H), 1.40–1.98 (m, 4H), 2.55–2.62 (m, 2H), 3.00–3.15 (m, 1H), 3.91–4.12 (m, 2H), 6.88 (s, 1H), 7.06 (s, 1H), 7.10–7.36 (m, 5H) and 7.47 (s, 1H).

(c) Ethyl 6-[1-(1H-imidazolyl-1-ylmethyl)-4-phenylbutyl thio]hexanoate

1-[1-(2-Mercapto-5-phenylpentyl)]-1H-imidazole (2.46 g, 0.01 mol), ethyl-6-bromohexanoate (4.46, 0.02 mol) potassium carbonate (5.52 g, 0.04 mol) and potassium iodide (180 mg, 0.001 mol) were stirred together in dimethylformamide (20 ml) for 3 h. at room temperature. The reaction mixture was diluted with ethyl acetate (200 ml), washed with water, dried (MgSO$_4$) and solvent removed at reduced pressure. The pure product was isolated by column chromatography (silica gel, chloroform) as a pale yellow oil.

$^1$H-NMR ($\delta$-CDCl$_3$): 1.25 (t, 3H), 1.27–1.98 (m, 10H), 2.20–2.33 (m, 4H), 2.51–2.71 (m, 2H), 2.71–2.85 (m, 1H), 3.92–4.07 (m, 2H), 4.14 (q, 2H), 6.90 (s, 1H), 7.04 (s, 1H), 7.13–7.30 (m, 5H) and 7.48 (s, 1H).

1-[2-(4-Methoxyphenyl)-methylthio]-5-phenylpentyl]-1H-imidazole

1-[1-(2-Mercapto-5-phenylpentyl)]-1H-imidazole (Example 44b) (2.46 g, 0.01 mol), 4-methoxybenzyl chloride (3.12 g, 0.02 mol) and potassium carbonate (5.52 g, 0.04 mol) were stirred together in dimethylformamide (20 ml) at room temperature for 12 h. The reaction mixture was diluted with ethyl acetate (200 ml), washed with water (5×200 ml), dried (MgSO$_4$) and solvent removed at reduced pressure. The product was isolated by column chromatography (silica gel, chloroform) as a colourless oil.

$^1$H-NMR ($\delta$-CDCl$_3$): 1.30–1.91 (m, 4H), 2.41–2.58 (m, 2H), 2.59–2.73 (m, 1H), 3.28–3.49 (m, 2H), 3.77 (s, 3H), 3.88–3.98 (m, 2H) and 6.77–7.38 (m, 12H).

EXAMPLE 46

1-[2-[(4-Methoxyphenyl)ethyl]-3-[(4-methoxyphenyl)-methoxy]propyl]-1H-imidazole

(a) [4-(4-Methoxyphenyl)]-2-hyroxymethylbutanoic acid

To a solution of lithium diisopropylamide (prepared from diisopropylamine (16.16 g, 0.16 mol and n-butyl lithium (1.6M in hexane, 100 ml, 0.016 mol) in THF (50 ml) at −78° C., was added a solution of 4-(4-methoxyphenyl)butanoic acid (13.80 g, 0.07 mol) in THF (100 ml) over 20 min. The solution was warmed to −20° C. and stirred for 2.5 h. Formaldehyde gas generated by warming paraformaldehyde (10 g) was then passed into the reaction mixture in a stream of nitrogen. After stirring for a further 2 h. at −20° C., hydrochloric acid (2N, 500 ml) was added and the reaction mixture was diluted with ethyl acetate (800 ml). After washing with water, the organic phase was extracted with sodium hydroxide solution (0.5N, 3×200 ml). The combined aqueous extracts were acidified with hydrochloric acid and extracted with ethyl acetate (3×200 ml), the combined organic phase (MgSO$_4$) was dried and solvent removed at reduced pressure to give the product as a colourless solid.

$^1$H-NMR (δ-CDCl$_3$): 1.70–2.05 (m, 2H), 2.56–2.68 (m, 3H), 3.75 (s, 3H), 3.72–3.86 (m, 2H) 6.82 and 7.09 (ABq, 4H) and 8.01 (br.s, 2H).

(b) Methyl-[4-(4-methoxyphenyl)]-2-hydroxymethyl butanoate

A mixture of [4-(4-methoxyphenyl)]-2-hydroxymethyl butanoic acid (6.0 g, 0.027 mol), iodomethane (5.68 g, 0.04 mol) and potassium carbonate (7.45 g, 0.054 mol) in dimethylformamide (40 ml) was heated at 70° C. for 1 h. After cooling to room temperature the reaction mixture was diluted with ethyl acetate (400 ml), washed with water (3×200 ml), sodium hydrogen carbonate solution (2×200 ml) and again with water (2×200 ml). Drying (MgSO$_4$) and removal of solvent at reduced pressure gave the product as a pale yellow oil.

$^1$H-NMR (δ-CDCl$_3$): 1.72–2.03 (m, 2H) 2.39 (br.s, 1H), 2.54–2.66 (m, 3H), 3.72 (s, 3H), 3.73–3.81 (m, 2H) 3.79 (s, 3H) and 6.82 and 7.09 (ABq, 4H).

(c) Methyl-[4-(4-methoxyphenyl)]-2-methanesulphonyloxy-methyl butanoate

A solution of methyl-4[(4-methoxyphenyl)]-2-hydroxymethyl butanonate (3.90 g, 0.0173 mol), triethylamine (3.40 g, 0.034 mol) and dimethylaminopyridine (0.05 g, 0.04 mol) in dichloromethane (30 ml) was cooled to −20° C. and methanesulphonyl chloride (2.05 g, 0.018 mol) added over 5 min. After stirring for an additional 20 min. the solution was warmed to room temperature, washed with saturated ammonium chloride solution (2×50 ml) and water (2×50 ml). The organic phase was dried (MgSO$_4$) and the solvent removed at reduced pressure to give the product as a colourless oil.

$^1$H-NMR (δ-CDCl$_3$): 1.74–2.07 (m, 2H), 2.61 (t, 2H), 2.77–2.91 (m, 1H), 3.00 (s, 3H), 3.72 (s, 3H), 3.78 (s, 3H), 4.26–4.44 (m, 2H) and 6.83 and 7.09 (ABq, 4H).

(d) Methyl[4-(4-methoxyphenyl)]-2-(1H-imidazol-1-ylmethylbutanoate

A solution of methyl-[4-(4-methoxyphenyl)]-2-methane-sulphonyloxymethyl butanoate (5.4 g, 0.017 mol) and imidazole (10 g, 0.149 mol) was heated to reflux in acetonitrile (40 ml) for 8 h. After cooling to room temperature the solvent was removed at reduced pressure, the residue dissolved in ethyl acetate (200 ml) and washed with water (5×200 ml). After drying (MgSO$_4$) and removal of solvent at reduced pressure, the residue was column chromatographed (silica gel, chloroform) to give the product as an oil.

$^1$H-NMR (δ-CDCl$_3$): 1.67–2.06 (m, 2H), 2.47, 2.47–2.69 (m, 2H), 2.74–2.89 (m, 1H), 3.64 (s, 3H), 3.78 (s, 3H), 3.95–4.27 (m, 2H), 6.78–6.93 (m, 3H), 6.99–7.11 (m, 3H) and 7.41 (s, 1H).

(e) 1-[2-[(4-Methoxyphenyl)ethyl]-3-hyroxypropyl]-1H-imidazole

A solution of methyl[4-(4-methoxyphenyl)-2-(1H-imidazol-1-ylmethyl)]butanoate (2.30 Lg, 0.08 mol) in ether 20 ml, at 0° C., was treated with lithium aluminium hydride (300 mg, 0.08 mol) over 5 min. After stirring for a further 1 h. at 0° C., saturated aqueous ammonium chloride was added cautiously to destroy excess lithium aluminium hydride. After filtration and drying (MgSO$_4$) the solvent was removed at reduced pressure to give the crude product as an oil suitable for use in the next stage.

$^1$H-NMR (δ-CDCl$_3$): 1.46–1.79 (m, 2H), 1.83–1.99 (m, 1H), 2.50–2.75 (m, 2H), 3.47 (d, 2H), 3.76 (s, 3H), 3.91–4.11 (m, 2H), 6.80 and 7.05 (ABq, 4H), 6.88 (s, 1H), 6.96 (s, 1H) and 7.42 (s, 1H).

(f) 1-[2-[(4-Methoxyphenyl)ethyl]-3-[(4-methoxyphenyl)-methoxy]propyl]-1H-imidazole This compound was prepared as in Example 30 using 1-[2-[(4-methoxyphenyl)ethyl]-3-hydroxypropyl]-1H-imidazole. The crude product was purified by column chromatography (silica gel, chloroform) to give the title compound as a colourless oil.

$^1$H-NMR (δ-CDCl$_3$): 1.46–1.72 (m, 2H), 1.89–2.02 (m, 1H), 2.45–2.74 (m, 2H), 3.26 (d, 2H), 3.78 (s, 3H), 3.82 (s, 3H), 3.88–4.09 (m, 2H), 4.33–4.46 (m, 2H), 6.73–7.08 (m, 8H) and 7.19–7.42 (m, 3H).

EXAMPLE 47

1-[5-(4-Methoxyphenyl)-2-[2-(4-methoxyphenyl)ethyl]-pent-1-yl]1H-imidazole

(a) 5-(4-Methoxyphenyl)-2-[2-(4-methoxyphenyl)ethyl]-pentanoic acid

A solution of diisopropylamine (15 g, 0.148 mol) in dry tetrahydrofuran (100 ml) at −78° C. was treated dropwise with a solution of butyl lithium in hexane (100 ml of a 1.6M solution 0.16 mol) under an atmosphere of dry argon. The solution was allowed to warm up to 0° C. over 2 hours, cooled back to −78° C. and treated with a solution of 4-(4-methoxyphenyl)butyric acid (14.1 g, 0.0726 mol) in dry tetrahydrofuran (50 ml). The solution was allowed to warm up to −20° C., cooled back to −78° C. and treated dropwise over 2 hours with 3-(4-methoxyphenyl)propyl chloride (13.5 g, 0.0731 mol). The solution was allowed to warm up to room temperature, poured into excess 2N hydrochloric acid and extracted with chloroform. The combined extracts were dried (MgSO$_4$) and the solvent was evaporated off under reduced pressure to give the crude product, which was further purified by column chromatography (silica gel, 50% chloroform in hexane) to give 5-(4-methoxyphenyl)-2-[2-(4-methoxyphenyl)ethyl]pentanoic acid as a colourless crystalline solid, m.p. 91°–94° C. (from toluene).

(b) 5-(4-Methoxyphenyl)-2-[2-(4-methoxyphenyl)ethyl]-1-pentanol

A solution of 5-(4-methoxyphenyl)-2-[2-(4-methoxyphenyl)ethyl]pentanoic acid (20 g, 0.058 mol) in dry tetrahydrofuran (50 ml) was treated with a solution of diborane in tetrahydrofuran (100 ml of 1M, 0.1 mol) and left to stand at room temperature for 10 hours. The solvent was evaporated off under reduced pressure and the residue was acidified with hydrochloric acid (2N) and extracted with chloroform. The combined extracts were dried (Na$_2$SO$_4$) and the solvent was evaporated off under reduced pressure to give the crude product which was further purified by column chromatography (silica gel, ethyl acetate) to give 5-(4-methoxyphenyl)-2-[2-(4-methoxyphenyl)ethyl]-1-pentanol as a colourless oil.

(c)
1-[5-(4-Methoxyphenyl)-2-[2-(4-methoxyphenyl)ethyl]-pent-1-yl]-1H-imidazole

A solution of 5-(4-methoxyphenyl)-2-[2-(4-methoxyphenyl)ethyl]-1-pentanol (9.5 g, 0.029 mol) in dry pyridine (100 ml) at 0° C. was treated dropwise with methanesulphonyl chloride (3.5 g, 0.0306 mol). The reaction was stirred at 0° C. for 2 hours and then at room temperature for a further 12 hours. A solution of imidazole sodium salt (5.4 g, 0.06 mol) in dry dimethylformamide (100 ml) was then added dropwise and the mixture was stirred for 3 hours. The solvent was evaporated off under reduced pressure and the crude product was purified by column chromatography (silica gel, 2% ethanol in dichloromethane) to give 1-[5-(4-methoxyphenyl)-[2-(4-methoxyphenyl)ethyl]pent-1-yl]-1H-imidazole as an oil. The free base was dissolved in dichloromethane and acidified with ethereal hydrogen chloride. The solvent was evaporated off under reduced pressure and the residue was recrystallised from dichloromethane-pentane to give 1-[5-(4-methoxyphenyl)-2-[2-(4-methoxyphenyl)ethyl]pent-1-yl]-1H-imidazole, hydrochloride, as colourless needles (m.p. 117°–118° C.).

$^1$H-NMR ($\delta$-CDCl$_3$): 1.1–2.0 (m, 7H), 2.30–2.75 (m, 4H), 3.77 (s, 6H), 4.1–4.4 (m, 2H), 6.6–7.1 (m, 10H), 7.28 (s, 1H), and 9.60 (s, 1H).

EXAMPLE 48

1-[2-[(4-Methoxyphenyl)methoxy]-3-[(4-methoxyphenyl)methoxy]propyl]-1H-morpholine (c)
1-[2-Hydroxy-3-(4-methoxyphenyl)methoxy]propyl]-1H-morpholine 2,3-Epoxypropyl-4-methoxybenzyl ether (16 g, 0.082 mol) in dry tetrahydrofuran (100 ml) was treated with morpholine (10 g, 0.11 mol) and stirred at ambient temperature for 48 hrs. The resulting mixture was filtered and the filtrate was evaporated to dryness under reduced pressure to give the crude product. Further purification of the crude product by column chromatography (silica gel, 50% hexane in chloroform) afforded 1-[2-hydroxy-3-(4-methoxyphenyl)methoxy]propyl]-1H morpholine as a pale yellow oil.

$^1$H-NMR ($\delta$-CDCl$_3$): 2.36–2.52 (m, 4H), 2.81 (broad s, 1H), 3.53–3.74 (m, 9H), 3.79 (s, 3H), 4.47 (s, 2H), 6.85–7.31 (m, 4H).

(b)
1-[2-[(4-Methoxyphenyl)methoxy]-3-[(4-methoxyphenyl)methoxy]propyl]-1H-morpholine Potassium t-butoxide (2.30 g, 0.021 mol) was added to a stirred solution of 1-[2-hydroxy-3-(4-methoxyphenyl)methoxy]-propyl]-1H-morpholine (5.46 g, 0.020 mol) in dry tetrahydrofuran (50 ml) under an atmosphere of dry nitrogen. After 1 hour, 4-methoxybenzyl chloride (3.13 g, 0.020 mol) was added and the solution was stirred for a further 24 hours. The solvent was evaporated off under reduced pressure and the residue was treated with water (200 ml) and extracted with chloroform. The combined extracts were dried (MgSO$_4$) and the solvent was evaporated off under reduced pressure to give the crude product which was further purified by column chromatography (silica gel, chloroform) to give 1-[2-[4-methoxyphenyl)methoxy]-3-[(4-methoxyphenyl)-methoxy]propyl]-1H-morpholine as a pale yellow oil.

$^1$H-NMR ($\delta$-CDCl$_3$): 2.36–2.52 (m, 4H), 3.53–3.74 (m, 9H), 3.79 (s, 3H), 4.47 (s, 2H), 4.59 (s, 2h), and 6.89–7.31 (m, 8H).

EXAMPLE 49

1-(2-[(4-Methoxyphenyl)methoxy]-3-[(4-carboethoxyphenyl)methoxy]propyl)-3-pyridine (a)
1-([(4-Methoxyphenyl)methoxy]methyl)-2-(3-pyridyl)ethanol 3-Bromopyridine (3.5 g, 0.022 mol) in dry tetrahydrofuran (5 ml) was added dropwise to a stirred solution of t-butyllithium (1.4M, 15.7 ml, 0.022 mol) in dry tetrahydrofuran (100 ml) at −100° C. under nitrogen atmosphere. The resultant solution was stirred for 20 min and cuprous iodide-trimethyl phosphite complex (6.9 g, 0.022 mol) in dry tetrahydrofuran (15 ml) added. After a further 10 min, 2,3-epoxypropyl-4-methoxybenzyl ether (4.27 g, 0.022 mol) in dry tetrahydrofuran (10 ml) was added and the mixture allowed to warm up from −100° to 20° C. over 3 hours and left to stir overnight at room temperature. The mixture was quenched with saturated aqueous ammonium chloride and evaporated in vacuo. The solid was extracted with ethyl acetate (300 ml), washed with water and dried (MgSO$_4$). Filtration and evaporation of solvent in vacuo gave a crude oil which was purified by column chromatography (silica gel/chloroform). Recrystallisation from ether/pentane gave pure 1-(3-pyridyl)-3-[(4-methoxyphenyl)-methoxy]propan-2-ol as a colourless crystalline solid, m.p. 55°–56°.

$^1$H-NMR ($\delta$-CDCl$_3$): 2.78 (d, 3H), 3.27–3.55 (m, 2H), 3.81 (s, 3H), 4.00 (m, 1H), 4.48 (s, 2H), 6.89 (d, 2H), 7.15–7.40 (m, 3H), 7.55 (d, 1H) and 8.45 (br.s, 2H).

(b)
1-(2-[(4-Methoxyphenyl)methoxy]-3-[(4-carboethoxyphenyl)methoxy]propyl)-3-pyridine This compound was prepared as described in Example 30 but using 1-([(4-methoxyphenyl)methoxy]methyl]-2-(3-pyridyl)ethanol. The crude product was purified by column chromatography (silica gel, 10% ethanol in chloroform) to give the title compound as a clear viscous colourless oil.

$^1$H-NMR ($\delta$-CDCl$_3$): 1.39 (t, 3H), 2.78–2.96 (m, 2H), 3.5 (d, 2H), 3.70–3.80 (m, 1H), 3.81 (s, 3H), 4.37 (q, 2H), 4.47 (s, 2H), 4.48 (d, 2H), 4.65 (d, 2H), 6.88 (d, 2H), 7.10–7.30 (m, 5H), 7.49 (d, 1H), 7.94 (d, 2H) and 8.47 (br.s, 2H).

EXAMPLE 50

1-(2-[(4-Methoxyphenyl)methoxy]-3-[(4-carboxyphenyl)methoxy]propyl)-3-pyridine

Example 49b (0.6 g, 1.4 mmol) was hydrolysed by treatment with a solution of sodium hydroxide (1 g) in methanol (10 ml) and water (1 ml) at 70° C. for 0.5 hours. The resultant mixture was evaporated under reduced pressure, taken up in ethyl acetate and water and brought to pH7 with 6N HCl. The organic layer was separated, washed with brine, dried (MgSO$_4$), filtered and evaporated in vacuo to give a crude oil. Purification by column chromatography (silica gel, 10% MeOH/CHCl$_3$) and crystallisation from ether/pentane gave the title compound as a colourless crystalline solid m.p. 117°–119°.

$^1$H-NMR (δ-CDCl$_3$): 2.75–3.00 (m, 2H), 3.45–3.65 (m, 2H), 3.68–3.85 (m, 1H), 3.82 (s, 3H), 4.40 (d, 2H), 4.52 (s, 2H), 4.70 (d, 2H), 6.90 (d, 2H), 7.19 (d, 2H), 7.25–7.35 (m, 3H), 7.60 (d, 1H), 8.04 (d, 2H), 8.53 (s, 1H) and 8.59 (d, 1H).

EXAMPLE 51

1-[2-[(4-Methoxyphenyl)methoxy]-3-[(4-methoxyphenyl)methoxy]propyl]-3-pyridine

The title compound was prepared as described in Example 30 but using 1-([(4-methoxyphenyl)methoxy]-methyl)-2-(3-pyridyl)ethanol, (Example 49a). The crude product was purified by column chromatography (silica gel, 10% ethanol in chloroform) to give the title compound as a clear, colourless, viscous oil.

$^1$H-NMR (δ-CDCl$_3$): 2.70–2.95 (m, 2H), 3.35–3.55 (m, 2H), 3.65–3.85 (m, 1H), 3.78 (s, 3H), 3.80 (s, 3H), 4.34 (d, 2H), 4.67 (s, 2H), 4.51 (d, 2H), 6.80 (d, 2H), 6.88 (d, 2H), 7.00–7.30 (m, 5H), 7.48 (d, 1H) and 8.46 (br.s, 2H).

EXAMPLE 52

1-(2-[(4-Methoxyphenyl)methoxy]-3-[(4-carboethoxyphenyl)methoxy]propyl)-4-pyridine (a)

1-([(4-Methoxyphenyl)methoxy]methyl)-2-(4-pyridyl)ethanol

The title compound was prepared as described in Example 49a but using 4-bromopyridine. The title compound was isolated as a white crystalline solid, m.p. 67°–68° C.

$^1$H-NMR (δ-CDCl$_3$): 2.76 (d, 2H), 2.87 (br.s, 1H, D$_2$O exchangeable), 3.31–3.49 (m, 2H), 3.80 (s, 3H), 4.05 (m, 1H), 4.46 (s, 2H), 6.87 (d, 2H), 7.14 (br.s, 2H), 7.23 (d, 2H) and 8.46 (br.s, 2H).

(b)

1-(2-[(4-Methoxyphenyl)methoxy]-3-[(4-carboethoxyphenyl)methoxy]propyl)-4-pyridine The title compound was prepared as described in Example 30 but using 1-([(4-methoxyphenyl)methoxy]-methyl)-2-(4-pyridyl)ethanol. The crude product was purified by column chromatography (silica gel, 10% ethanol in chloroform) to give the title compound as a colourless, clear, viscous oil.

$^1$H-NMR (δ-CDCl$_3$): 1.40 (t, 3H), 2.77–3.00 (m, 2H), 3.50 (d, 2H), 3.70–3.90 (m, 1H), 3.82 (s, 3H), 4.37 (q, 2H), 4.47 (s, 2H), 4.49 (d, 2H), 4.67 (d, 2H), 6.89 (d, 2H), 7.10 (d, 2H), 7.17–7.32 (m, 4H), 7.97 (d, 2H) and 8.50 (d, 2H).

EXAMPLE 53

Methyl 6-[2-(b 1H-imidazol-1-yl)-1-[[(4-methoxyphenyl)methoxy]methyl]ethoxy]-(E)-pent-2-enoate (a)

1-[2-(3-hydroxypropyl)oxy]-3-[(4-methoxyphenyl)methoxy]propyl]-1H-imidazole

To a solution of 1-[2-(prop-2-enyl)oxy]-3-[(4-methoxyphenyl)methoxy]propyl]-1H-imidazole (Example 17) (13.0 g, 0.043 mol) in tetrahydrofuran (100 ml) at 0° C. under nitrogen, a solution of 9-borabicyclo [3.3.1] nonane (6.1 g 0.05 mol) in tetrahydrofuran (50 ml) was added over 10 mins. After the addition was complete the reaction mixture was stirred at room temperature for 1h and subsequently at 70° C. for 2 h. The reaction mixture was then cooled to 0° C., and treated sequentially with ethanol (30 ml), aqueous sodium hydroxide (6N, 10 ml) and finally with hydrogen peroxide (30%, 20 ml). After stirring for 1 h at 0° C., potassium carbonate was added to remove water, and the reaction mixture filtered. The filtrate was evaporated to dryness at reduced pressure and the residue column chromatographed (silica gel, chloroform) to give the title compound as a pale yellow oil.

$^1$H-NMR (δ-CDCl$_3$): 1.64–1.81 (m, 2H), 3.27–3.51 (m, 3H), 3.55–3.69 (m, 4H), 3.81 (s, 3H), 3.94–4.19 (m, 2H), 4.46 (s, 2H), 6.89 and 7.26 (ABq, 4H), 6.91 (s, 1H), 7.02 (s, 1H) and 7.48 (s, 1H).

(b)

1-[2-(3-Oxopropyl)oxy]-3-[(4-methoxyphenyl)methoxy]propyl]-1H-imidazole

Oxalyl chloride (1.01 g, 0.008 mol) in dichloromethane (20 ml) at −78° C. was treated with dimethylsulphoxide (1.39 g, 0.018 mol) in dichloromethane (10 ml) over 2 min. After stirring at −78° C. for 5 min, a solution of 1-[2-(3-hydroxypropyl)oxy]-3-[(4-methoxyphenyl)methoxy]propyl]-1H-imidazole (2.04 g, 0.0064 mol) in dichloromethane (5 ml) was added. Stirring was continued for a further 20 mins, after which time triethylamine (7 ml, 0.051 mol) was added and the reaction mixture allowed to warm to room temperature over 2 h. After washing with water and drying (MgSO$_4$), solvent was removed at reduced pressure and the residue column chromatographed (silica gel, chloroform) to give the title compound as a pale yellow oil.

$^1$H-NMR (δ-CDCl$_3$): 2.59 (dt, 2H), 3.22–3.54 (m, 2H), 3.55–3.72 (m, 2H), 3.76–3.91 (m, 1H), 3.80 (s, 3H), 3.91–4.16 (m, 2H), 4.46 (s, 2H), 6.89 and 7.25 (ABq, 4H), 6.91 (s, 1H), 7.02 (s, 1H), 7.45 (s, 1H) and 9.67 (t, 1H).

(c) Methyl 6-[2-(1H-imidazol-1-yl)-1-[[(4-methoxyphenyl)methoxy]methyl]ethoxy]-(E)-pent-2-enoate A solution of 1-[2-(3-oxopropyl)oxy]3-[(4-methoxyphenyl)methoxy]propyl]-1H-imidazole (640 mg, 0.002 mol) in tetrahydrofuran (5 ml) containing carbomethoxymethylene triphenylphosphorane (1.67 g, 0.005 mol) was stirred at room temperature for 12 h. The solvent was then removed in vacuo, the residue taken up in ethyl acetate washed with water and extracted with 1N hydrochloric acid. The combined acid extracts were washed with ethyl acetate, neutralised with solid sodium hydrogen carbonate and extracted with ethyl acetate. The combined organic extracts were washed with saturated brine, dried (MgSO$_4$) and column chromatographed (silica gel, 20% hexane in chloroform) to give the title compound as a colourless oil.

$^1$H-NMR (δ-CDCl$_3$): 2.35–2.47 (m, 2H), 3.25–3.69 (m, 5H), 3.74 (s, 3H), 3.82 (s, 3H), 3.91–4.19 (m, 2H), 4.45 (s, 2H), 5.81–5.92 (m, 1H), 6.80–6.97 (m, 4H), 7.03 (s, 1H), 7.25 (d, 2H) and 7.44 (s, 1H).

EXAMPLE 54

Ethyl 6-[2-(1H-imidazol-1-yl)-1-[[(4-methoxyphenyl)methoxy]methyl]propoxy]hexanoate (a) 2,3-epoxy-2-methylpropyl-4-methoxybenzyl ether This compound was prepared as in Example 1a but using 2-chloromethyl-2-methyl oxirane. The product was used without further purification (Example 54b).

(b) 1-[2-Hydroxy-2-methyl-3-[(4-methoxyphenyl)methoxy]propyl]-1H-imidazole

This compound was prepared as in Example 1b but using 2,3-epoxy-2-methylpropyl-4-methoxybenzyl ether. The crude product was purified by column chromatography (silica gel, chloroform) to give the tite compound as a colourless oil.

$^1$H-NMR ($\delta$-CDCl$_3$): 1.15 (s, 3H), 3.18–3.26 (m, 2H), 3.79 (s, 3H), 3.95 (q, 2H), 4.40–4.50 (m, 2H), 4.69 (br.s, 1H), 6.83–6.93 (m, 4H), 7.24 (d, 2H) and 7.40 (s, 1H).

(c) Ethyl 6-[2-(1H-imidazol-1-yl)-1-[[(4-methoxyphenyl)methoxy]methyl]propoxy]hexanoate To a solution of 1-[2-hydroxy-2-methyl-3-[(4-methoxyphenyl)methoxy]propyl]-1H-imidazole (3.2 g, 0.0116 mol) in dimethylsulphoxide (20 ml) at 10° C., potassium tert butoxide (2.1 g, 0.018 mol) was added in portions over 10 min. CAUTION (see, L. Bretherick, Royal Society of Chemistry, Hazards in the Chemical Laboratory, 3rd Ed. p. 307). After stirring for 5 mins. a solution of ethyl 6-bromohexanoate (2.58 g, 0.0116 mol) in dimethyl sulphoxide (5 ml) was added, the reaction mixture warmed to room temperature, and stirring continued for a further 45 min. The mixture was poured into water, neutralised with 1N hydrochloric acid and extracted with dichloromethane. The combined organic extracts were washed with water, dried (MgSO$_4$) and solvent removed at reduced pressure. The title compound was isolated by column chromatography (silica gel, 3% ethanol in chloroform) as a yellow oil.

$^1$H-NMR ($\delta$-CDCl$_3$): 1.12 (s, 3H), 1.26 (t, 3H), 1.31–1.70 (m, 6H), 2.30 (t, 2H), 3.19 (q, 2H), 3.27–3.41 (m, 2H), 3.82 (s, 3H), 3.91–4.02, (m, 2H), 4.13 (q, 2H), 4.37–4.48 (m, 2H), 6.89 and 7.25 (ABq, 4H), 6.90 (s, 1H) 7.00 (s, 1H) and 7.45 (s,1H).

We claim:

1. A compound of the formula

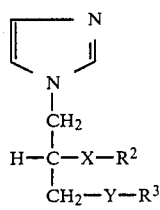

wherein
X represents —O—, —S—, —NR$^1$— or —CH$_2$— wherein R$^1$ is hydrogen or C$_1$–C$_6$ alkyl;
Y represents —O—, —S— or —CH$_2$—;
R$^2$ represents C$_1$–C$_{10}$ alkyl terminally substituted with a —COOR$^1$ group wherein R$^1$ is hydrogen or C$_1$–C$_6$ alkyl; and
R$^3$ represents hydrogen, C$_1$–C$_{10}$ straight or branched chain alkyl which may be terminally substituted with OR$^1$ or SR$^1$ wherein R$^1$ is hydrogen or C$_1$–C$_6$ alkyl; or a —CH$_2$R$^5$ group wherein R$^5$ represents phenyl or phenyl substituted with one substituent selected from the group consisting of halogen, —OR$^1$, —(S=O)$_n$R$^1$ (n=0-2), —COR$^1$, —COOR$^1$, —CONHR$^1$, —CON(R$^1$)$_2$, —NHR$^1$ or —N(R$^1$)$_2$ wherein R$^1$ is hydrogen or C$_1$–C$_6$ alkyl; and pharmaceutically acceptable salts thereof.

2. A compound according to claim 1 wherein R$^3$ is a —CH$_2$R$^5$ group wherein R$^5$ represents phenyl or phenyl substituted with one or more substituents selected from the group consisting of halogen, —OR$^1$, —(S=O)$_n$R$^1$ (n=0-2), —COR$^1$, —COOR$^1$, —CONHR$^1$, —CON(R$^1$)$_2$, —NHR$^1$ or —N(R$^1$)$_2$.

3. A compound according to claim 2 2,2-dimethyl-6-[2-(1H-imidazol-1-yl)-1-[[(4-methoxyphenyl)methoxy]methyl]ethoxy]hexanoic acid having the formula

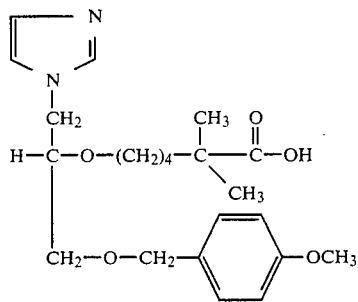

4. A pharmaceutical composition comprising a therapeutically effective dosage of an active ingredient of the formula

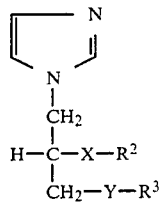

wherein
X represents —O—, —S—, —NR$^1$— or —CH$_2$— wherein R$^1$ is hydrogen or C$_1$–C$_6$ alkyl;
Y represents —O—, —S— or —CH$_2$—;
R$^2$ represents C$_1$–C$_{10}$ alkyl terminally substituted with a —COOR$^1$ group wherein R$^1$ is hydrogen or C$_1$–C$_6$ alkyl; and
R$^3$ represents hydrogen, C$_1$–C$_{10}$ straight or branched chain alkyl which may be terminally substituted with OR$^1$ or SR$^1$ wherein R$^1$ is hydrogen or C$_1$–C$_6$ alkyl; or a —CH$_2$R$^5$ group wherein R$^5$ represents phenyl or phenyl substituted with one substituent selected from the group consisting of halogen, —OR$^1$, —(S=O)$_n$R$^1$ (n=0-2), —COR$^1$, —COOR$^1$, —CONHR$^1$, —CON(R$^1$)$_2$, —NHR$^1$ or —N(R$^1$)$_2$ wherein R$^1$ is hydrogen or C$_1$–C$_6$ alkyl; and pharmaceutically acceptable salts thereof; and a pharmaceutically acceptable carrier or diluent.

5. A pharmaceutical composition according to claim 4 having from 5 to 250 mg of the active ingredient.

6. A method of treating a patient suffering from a condition susceptible to treatment with an antithrombotic agent comprises administering to the patient a therapeutically effective amount of a compound of the formula

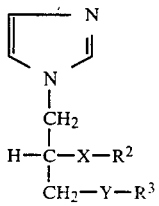

wherein

X represents —O—, —S—, —NR$^1$— or —CH$_2$— wherein R$^1$ is hydrogen or C$_1$-C$_6$ alkyl;

Y represents —O—, —S— or —CH$_2$—;

R$^2$ represents C$_1$-C$_{10}$ alkyl terminally substituted with a —COOR$^1$ group wherein R$^1$ is hydrogen or C$_1$-C$_6$ alkyl; and R$^3$ represents hydrogen, C$_1$-C$_{10}$ straight or branched chain alkyl which may be terminally substituted with OR$^1$ or SR$^1$ wherein R$^1$ is hydrogen or C$_1$-C$_6$ alkyl; or a —CH$_2$R$^5$ group wherein R$^5$ represents phenyl or phenyl substituted with one substituent selected from the group consisting of halogen, —OR$^1$, —(S=O)$_n$R$^1$ (n=0-2), —COR$^1$, —COOR$^1$, —CONHR$^1$, —CON(R$^1$)$_2$, —NHR$^1$ or —N(R$^1$)$_2$ wherein R$^1$ is hydrogen or C$_1$-C$_6$ alkyl; and pharmaceutically acceptable salts thereof.

7. The compound as claimed in claim 2, which is 6-[2-(1H-Imidazol-1-yl)-1-[[(4-methoxyphenyl)methoxy]methyl]ethoxy]hexanoic acid.

8. The compound as claimed in claim 2, which is 5-[2-(1H-Imidazol-1-yl)-1-[[(4-methoxyphenyl)methoxy]methyl]ethoxy]pentanoic acid.

9. The compound as claimed in claim 2, which is Ethyl 6-[2-(1H-imidazol-1-yl)-1-[[(4-methoxyphenyl)-methoxy]methyl]ethoxy]hexanoate.

10. The compound as claimed in claim 2, which is Ethyl 5-[2-(1H-imidazol-1-yl)-1-[[(4-methoxyphenyl)-methoxy]methyl]ethoxy]pentanoate.

11. The compound as claimed in claim 1, which is Neopentyl 6-[2-(1H-imidazol-1-yl)-1-[[(4-methoxyphenyl)methoxy]methyl]ethoxy]hexanoate.

12. The compound as claimed in claim 1, which is Ethyl 6-[2-(1H-imidazol-1-yl)-1-[[(4-bromophenyl)methoxy]methyl]ethoxy]hexanoate.

13. The compound as claimed in claim 1, which is 6-[2-(1H-Imidazolyl-1-yl)-1-[(phenylmethoxy)methyl]ethoxy]hexanoic acid.

14. A composition as claimed in claim 4 adapted for oral administration.

15. A composition as claimed in claim 14 in the form of a tablet or capsule, containing a specified quantity of active ingredient of formula I.

16. A composition as claimed in claim 15 in which the amount of active ingredient is within the range of 5 to 250 mg.

17. A composition as claimed in claim 4 adapted for injection.

* * * * *